US012398424B2

(12) United States Patent
Cottier

(10) Patent No.: US 12,398,424 B2
(45) Date of Patent: Aug. 26, 2025

(54) METHODS FOR DETERMINING KINETIC PARAMETERS OF A REACTION BETWEEN ANALYTE AND LIGANDS

(71) Applicant: Creoptix AG, Wädenswil (CH)

(72) Inventor: Kaspar Cottier, Wädenswil (CH)

(73) Assignee: Creoptix AG, Wädenswil (CH)

( * ) Notice: Subject to any disclaimer, the term of this patent is extended or adjusted under 35 U.S.C. 154(b) by 1046 days.

(21) Appl. No.: 17/431,193

(22) PCT Filed: May 12, 2020

(86) PCT No.: PCT/IB2020/054472
§ 371 (c)(1),
(2) Date: Aug. 16, 2021

(87) PCT Pub. No.: WO2020/234691
PCT Pub. Date: Nov. 26, 2020

(65) Prior Publication Data
US 2022/0162697 A1    May 26, 2022

(30) Foreign Application Priority Data

May 17, 2019  (CH) ......................................... 648/19

(51) Int. Cl.
| | |
|---|---|
| G01N 33/557 | (2006.01) |
| C12Q 1/6825 | (2018.01) |
| C12Q 1/6837 | (2018.01) |
| C12Q 1/6876 | (2018.01) |
| G01N 15/1434 | (2024.01) |
| G01N 15/10 | (2006.01) |

(52) U.S. Cl.
CPC ......... *C12Q 1/6876* (2013.01); *C12Q 1/6825* (2013.01); *C12Q 1/6837* (2013.01); *G01N 15/1436* (2013.01); *G01N 2015/1006* (2013.01)

(58) Field of Classification Search
None
See application file for complete search history.

(56) References Cited

U.S. PATENT DOCUMENTS

| | | |
|---|---|---|
| 7,858,372 B2 | 12/2010 | Whalen |
| 8,906,672 B2 | 12/2014 | Quinn |
| 9,851,347 B2 | 12/2017 | Cottier |
| 9,853,276 B2 | 12/2017 | Yasui et al. |
| 9,958,396 B2 | 5/2018 | Chou et al. |
| 9,990,464 B1 | 6/2018 | Quinn |
| 10,101,299 B2 | 10/2018 | Wang et al. |
| 10,458,984 B2 | 10/2019 | Karlsson |
| 10,725,030 B2 | 7/2020 | Karlsson |
| 11,135,581 B2 | 10/2021 | Cottier |

(Continued)

FOREIGN PATENT DOCUMENTS

| | | |
|---|---|---|
| CN | 102652259 A | 8/2012 |
| CN | 103582813 A | 2/2014 |

(Continued)

OTHER PUBLICATIONS

International Search Report and Written Opinion for PCT/IB2020/054472 dated Aug. 11, 2020, 11 pgs.
J. J. Bowling, et al., "Going Small: Using Biophysical Screening to Implement Fragment Based Drug Discovery", Special Topics in Drug Discovery, http://dx.doi.org/10.5772/66423; 30 pgs., © 2016, pp. 25-51.
A. M. Giannetti, et al., "Getting the Most Value from Your Screens: Advances in Hardware, Software, and Methodologies to Enhance Surface Plasmon Resonance Based Fragment Screening and Hit-to-Lead Support", Fragment-Based Drug Discovery, Royal Society of Chemistry, http://ebookcentral.proquest.com/lib/epo-ebooks/detail.action?docID=4095655; 2015; pp. 19-48.

(Continued)

*Primary Examiner* — Christopher M Gross
(74) *Attorney, Agent, or Firm* — BLANK ROME LLP

(57) ABSTRACT

According to the present invention there is provided a method for determining kinetic parameters of a reaction between analyte and ligands, the method comprising the steps of, a) flowing a first volume of sample fluid (V1), which has a concentration (co) of analytes, over a test surface (3) of a flow cell (2) which has first ligands (4) attached thereto, for a first time period (tia); b) flowing a first volume of buffer solution (X/Γ) over the test surface (3) of the flow cell (2), for a first time period (tib); c) flowing at least a second volume of sample fluid (V2), over the test surface, for a second time period (t2a); wherein the second time period (t2a) is greater than the first time period (tia) and wherein the second volume of sample fluid (V2) has the same concentration (c0) of analytes as the concentration (c0) of analytes in the first volume of sample fluid (V2); d) flowing a second volume of buffer solution (V2') over the test surface (3) of the flow cell (2), for a second time period (t2b); e) using a sensor to measure the binding on the test surface (3) during steps (a)-(d) to obtain a single measurement binding curve; f) flowing a first volume of sample fluid (V1), which has a concentration (Co) of analytes, over a test surface (3') of a flow cell (2') which is without first ligands, for a first time period (tia); g) flowing a first volume of buffer solution (X/Γ) over the test surface (3') which is without first ligands, for a first time period (fib); h) flowing at least a second volume of sample fluid (V2), over the test surface (3') which is without first ligands, for a second time period (t2a); wherein the second time period (t2a) is greater than the first time period (t1a) and wherein the second volume of sample fluid (V2) has the same concentration (c0) of analytes as the concentration (c0) of analytes in the first volume of sample fluid (V2); i) flowing a second volume of buffer solution (V2') over the test surface (3) which is without first ligands, for a second time period (t2b); J) using a sensor to measure the binding on the test surface (3) which is without first ligands, during steps (f)-(i), to obtain a single reference binding curve; k) Using the single measurement binding curve and the single reference binding curve to determine the kinetic parameters.

20 Claims, 4 Drawing Sheets

(56) References Cited

U.S. PATENT DOCUMENTS

| | | |
|---|---|---|
| 11,255,851 B2 | 2/2022 | Karlsson |
| 11,287,424 B2 | 3/2022 | Ding et al. |
| 11,567,005 B2 | 1/2023 | Pol |
| 2003/0143565 A1 | 7/2003 | Trutnau |
| 2008/0033705 A1 | 2/2008 | Bynum et al. |
| 2014/0095082 A1 | 4/2014 | Kuderer |
| 2014/0141529 A1 | 5/2014 | Karlsson et al. |
| 2018/0224439 A1 | 8/2018 | Karlsson |
| 2018/0341624 A1 | 11/2018 | Soderman et al. |

FOREIGN PATENT DOCUMENTS

| | | |
|---|---|---|
| CN | 103620410 A | 3/2014 |
| CN | 104937418 A | 9/2015 |
| CN | 105181658 A | 12/2015 |
| CN | 107430123 A | 12/2017 |
| CN | 108139321 A | 6/2018 |
| CN | 108883414 A | 11/2018 |
| EP | 1631824 B1 | 4/2018 |
| GB | 2045929 A | 11/1980 |
| JP | 2006527365 A | 11/2006 |
| JP | 2010537194 A | 12/2010 |
| JP | 2015522151 A | 8/2015 |
| JP | 2017504805 A | 2/2017 |
| JP | 2018528431 A | 9/2018 |
| WO | WO-2009/025680 A1 | 2/2009 |
| WO | WO-2013/055281 A1 | 4/2013 |
| WO | WO-2014/009286 A1 | 1/2014 |
| WO | WO-2014/109284 A1 | 7/2014 |
| WO | WO-2015/114056 A1 | 8/2015 |
| WO | WO-2017/050940 A1 | 3/2017 |
| WO | WO-2017/187325 A1 | 11/2017 |

OTHER PUBLICATIONS

Office Action issued in related Chinese Patent Application No. 202080036463.7.

Office Action issued Aug. 17, 2023 in related Japanese Patent Application 2021-560907.

Inglese, James et al., "Quantitative high-throughput screening: A titration-based approach that efficiently identifies biological activities in large chemical libraries," PNAS, Aug. 1, 2006, vol. 103, No. 31, pp. 11473-11478.

METHODS FOR DETERMINING KINETIC PARAMETERS OF A REACTION BETWEEN ANALYTE AND LIGANDS

RELATED APPLICATIONS

This application is a national phase of PCT/IB2020/054472, filed on May 12, 2020, which claims the benefit of Swiss Application No. 00648/19, filed on May 17, 2019. The entire contents of these applications are hereby incorporated by reference.

FIELD OF THE INVENTION

The present invention concerns methods for method for determining kinetic parameters of a reaction between pre-defined molecules (i.e. analyte) and a target (i.e. ligands) and in particular, to methods which involve sequentially contacting a test surface of a flow cell which has said ligands attached thereto, with a plurality of sample fluid volumes each of which contain the same concentration of analyte; and evaluating an output of a sensor which measures binding on said test surface to determine said kinetic parameters.

DESCRIPTION OF RELATED ART

In many applications, such as drug discovery and development, environmental testing, and diagnostics, there is a need to analyse a large number of liquid samples in a short amount of time. Such analysis is performed using systems including, but not limited to, optical or acoustic label-free sensors or biosensors, mass spectrometers, chromatography systems, and spectrophotometric detectors.

Label-free acquisition methods include, but are not limited to, optical methods based on surface plasmon resonance (SPR) or waveguides, or methods based on surface-acoustic waves (SAW), thermal methods, or electro-chemical methods. Optical methods are based on the principle that biochemical molecules (i.e. analyte) exhibit a different refractive index than an aqueous solution. Refractive index changes near the sensor surface result from the addition or subtraction of molecules (i.e. analyte) to the surfaces due to the interaction of molecules (i.e. analyte) with either the sensor surface itself or another molecule attached to the surface. Using a resonant element—in case of SPR a metal layer supporting surface plasmons, or in case of waveguide sensors an optical waveguide supporting optical waveguide modes—the local refractive index changes can be then probed using an appropriate illumination and detection scheme, and the changes recorded in real time in order to measure the molecular reaction event. In this context, these changes correspond to the signal. Surface-Acoustic Wave and electro-chemical methods operate in a similar way, except that not the refractive index differences are physically measured, but rather mass or permittivity differences.

In this context, many label-free measurements or label-free sensing techniques or label-free assays involve attaching (immobilizing) of one or more "ligands" (a reactant such as antibodies or drug targets) to a solid support on a sensing surface (i.e. a sensitized surface on a sensor chip which is adapted to be read out by a detection scheme which outputs the measurements over time that compose the recorded signal). The fluid conduit containing the sensing surface is generally called flow cell or fluidic chamber and allows bringing a fluid containing the other reactant(s) to be investigated ("analyte") to be brought into contact with the ligand. Thereby the analyte has the opportunity to react with the immobilized ligands at the solid support on a sensing surface and an eventual product concentration is measured and characterized. A typical molecular interaction measurement procedure consists in first contacting the surface-bound ligand first with a neutral buffer solution ("buffer") in order to establish a base signal without reaction ("baseline"), followed by contacting the surface-bound ligand with a fluid containing the actual analyte or sample (such as an antigen or a drug candidate) so that the surface-bound ligand reacts with the analyte or sample, and the association phase where a reaction occurs can be monitored, and optionally followed by contacting the surface-bound ligand again with a neutral buffer solution in order to monitor the dissociation phase of the analyte or sample by removing the analyte from the flow cell. In other words, the concentration of the analyte is increased in a step-wise fashion for characterizing the association phase and decreased again in a step-wise fashion for characterizing the dissociation phase. The sensor signal recorded during association and dissociation phase is typically referred to as binding curve. Typically, the aforementioned steps are repeated for several concentrations of analyte, in order to generate a set of binding curves that can be fitted to an interaction model. Typically, during the whole time of the experiment, measurements are recorded, resulting in a reaction network signal, which may be further analyzed with the present invention to obtain the kinetic parameters.

Fluidic assemblies for delivering analytes from a sample reservoir to the flow cell are well known in the art, and typically comprise a sample storage and handling unit ("autosampler"), which is fluidly connected to a sample delivery unit comprising pumps, valves and conduits. Furthermore, it comprises a sequence controller unit which controls said autosampler, and the pumps and valves of the sample delivery unit, such as they are operated with an appropriate timing to execute a desired measurement method. Sample reservoirs can take the form of vials, or so-called "wells" within an industry-standardized container for multiple reservoirs ("microtiter plate"), typically containing 96, 384 or 1536 wells. Prior to a measurement, the microtiter plates are appropriately filled with analytes by the user or a fluid handling robot and then placed in the autosampler. During measurement, one or multiple analytes are aspirated from the microtiter plates by the autosampler, and then delivered or injected into the appropriate flow cell or flow cells by the sample delivery unit, such as the corresponding sensing surface(s) within the flow cell(s) are contacted with the analyte(s). The sample delivery unit is also adapted to rinse the appropriate flow cell or flow cells by injecting buffer such as the corresponding sensing surface(s) within the flow cell(s) are contacted with the buffer, allowing the analytes to dissociate from the ligands. Exemplary types of fluidic assemblies, which are adapted to implement the exemplary methods according to the method embodiments of the present invention, are described in WO2017187325.

Label-free acquisition methods relying on a refractive index change due to the presence of a substance are often susceptible to bulk refractive index mismatches, such as small differences in refractive index between the buffer and the fluid containing the sample. Such mismatches can cause an offset in the signal. To accurately compute the kinetic parameters from such a signal, the signal offset needs to be computed jointly with the kinetic parameters.

An exemplary type of optical waveguide-based biosensor is sold by Creoptix AG (Wädenswil, Switzerland) under the trade name WAVE® (hereinafter referred to as "the WAVE instrument"). These biosensors utilize a waveguide interferometry based mass-sensing technique to provide "real-time" sensor signals between a surface bound ligand and an analyte of interest. The WAVE instrument produces as output signal a sequence in time of density measurements in pg/mm2, density measurements which are proportional to the concentration of the product on the sensor surface.

Recently, the high throughput screening of molecular interactions has gained increased interest, in particular in pharmaceutical companies where drug to drug-target interactions are studied in drug discovery. During (high throughput) screening, typically a large number of analytes, which in this case are drug candidates, are prepared at a single concentration such as 100 micromolar or 100 nanomolar within an individual well, and successively injected into a flow cell comprising a ligand, which is in this case a drug target. Typically, in such a screening setting only binding levels, corresponding to a sensor signal value at a given time during injection, are evaluated from single injections. No reliable kinetic parameters can be extracted from measurements of single injections due to a strong correlation between unknown parameters, and therefore attempts at fitting the sensor signal for that single injection to an interaction model result in an ill-defined problem. In other words, the measurement of single injections of two analytes differing in kinetic parameters may produce similar binding curves. A candidate analyte is marked as a hit if the corresponding binding level falls within a certain range, such as between a minimum and a maximum, and if the shape of the binding does not show signs of non-specific interaction with the target or the surface. A major disadvantage of this method is that analytes which bind to ligands can not be well distinguished from artefacts such as bulk refractive index mismatches, and that no quantitative information about kinetic parameters can be determined. A hit then needs to be characterized for kinetic parameters in a successive measurement, typically using the method of injecting multiple concentrations from multiple wells. It is understood that using the method of injecting multiple concentrations from multiple wells is not adapted for primary screening, as the time for screening and preparing the analytes is increased, and the autosampler storage space is not well utilized.

A method for determining kinetic and affinity parameters of molecular interactions using an injection from a single well is described in WO2009025680 and currently marketed as OneStep injection by Molecular Devices (Danaher). It's application is described more in detail in A. M. Giannetti et al. Fragment-Based Drug Discovery, S. Howard, C. Abell, Eds. (Royal Soc. Chem., Cambridge, 2015) chap. 2. The method suffers from the limitation that the analysis time per sample is at least 30 seconds. Furthermore, while an indication of affinity can often be determined, the kinetic parameters can not be reliably determined. Furthermore, since the gradient profile is determined by the flow conduit geometry and the flow rate only, it is difficult to tailor the gradient profile to a specific kinetic range of interest.

A method for determining kinetic and affinity parameters of molecular interactions using sequential injections of analyte is described in WO2004109284. The method relies on providing different concentrations of an analyte, which makes the method not suited for screening applications.

The simplest model for molecular interaction is the Langmuir or 1:1 model with the reversible reaction $$A + B \rightleftharpoons AB, \tag{1}$$

where an analyte A and an immobilized ligand B reach equilibrium with the product AB. The reactants A and B associate to form the product AB, while simultaneously the reactant AB dissociates to form the products A and B. Hence, A, B and AB are simultaneously reactants and products.

Mathematically, the reaction network is described by the differential equations (a)
$$\frac{d[AB]}{dt} = k_a[A][B] - k_d[AB]$$

(b)
$$\frac{d[B]}{dt} = -k_a[A][B] + k_d[AB], \tag{2.}$$

where [A], [B] and [AB] are the concentrations of A, B and AB. The velocity of [A] and [B] associating to form the product [AB] is determined by the kinetic parameter $k_a$, and the velocity of [AB] dissociating to form the products [A] and [B] is determined by the kinetic parameter $k_d$. When expressing the reaction in terms of an observable sensor signal R which is proportional to [AB], as well as a maximum sensor signal Rmax which is proportional to the sum of the concentrations [B]+[AB], and the concentration c=[A], the reaction can be described by the differential equation $$\frac{dR}{dt} = k_a c (R_{max} - R) - k_d R. \tag{3}$$

Thus, the kinetic parameters of interest in a simple molecular interaction model are the so-called on-rate or association rate constant $k_a$, and the so-called off-rate or dissociation rate constant $k_d$. In a screening application, typically a region of interest within the kinetic space is selected by the researcher. In the example of early drug discovery, a researcher may choose that a valid drug candidate should exhibit a $k_a$ between $10^5$ $M^{-1}s^{-1}$ and $10^9$ $M^{-1}s^{-1}$, and a $k_d$ between $0.1$ $s^{-1}$ and $1000$ $s^{-1}$. In contrast, in the example of antibody screening, a researcher may choose that a valid candidate may exhibit a $k_a$ between $10^4$ $M^{-1}s^{-1}$ and $10^7$ $M^{-1}s^{-1}$, and a $k_d$ between $10^{-2}$ $s^{-1}$ and $10^{-6}$ $s^{-1}$. Typically, the measurable kinetic space depends on the device parameters, such as the measureable range, but also on the chosen measurement parameters such as contact times and concentrations. Hence, the researcher might choose this region of interest actively by selecting measurement parameters such as flowrates and analyte contact and dissociation times, or passively by choosing an appropriate measurement protocol which he knows that it works for his selected application.

Examples of higher throughput systems for screening applications include the Biacore® 8 k instrument, a method for operating which is described in WO2017050940, or the Sierra Sensors MASS-2 instrument, for which the flow cell configuration is described in U.S. Pat. No. 7,858,372B2. Both mentioned instruments are based on the effect of Surface Plasmon Resonance (SPR). However, the devices suffer from several limitations, such as high sample and buffer usage.

It is an aim of the present invention to mitigate at least some of the above-mentioned disadvantages. Some embodiments methods of present invention obviates the need for flowing multiple different concentrations of the analyte through the flow cell, which can advantageously lead to a reduced measurement time.

According to the invention, these aims are achieved by means of an assembly and/or method having the features recited in the independent claims; wherein the dependent claims recite optional features of preferred embodiments.

DETAILED DESCRIPTION OF POSSIBLE EMBODIMENTS OF THE INVENTION

The invention will be better understood with the aid of the description of the following embodiments which are given by way of example only, and illustrated by the figures.

While in the detailed description and Examples that follow, the present invention is illustrated in the context of waveguide interferometry, and more particularly the Creoptix WAVE system, it is to be understood that the present invention is not limited to this detection method. Rather, any affinity-based detection method where an analyte binds to a ligand immobilised on a sensing surface may be employed, provided that a change at the sensing surface can be measured which is quantitatively indicative of binding of the analyte to the immobilised ligand thereon.

In a preferred embodiment, ligands are immobilized using amine coupling within a thin hydrogel layer such as a Dextran or a polycarboxylate layer covalently bound to a sensor surface within a flow cell; in another preferred embodiment the ligands are captured by a suitable tag to a suitable capturing binding partner immobilized on the sensor surface, such as Polyhistidine tag to immobilized Nickel-Nitrilotriacetic acid (Ni-NTA) or Biotin tag to immobilized Streptavidin or AviTag™ tag to immobilized Streptavidin.

Typical ligands that can be used in the present invention include, but are not limited to, proteins (e.g., antibodies, affibodies, or aptamers), enzymes, receptors, antigens, haptens, peptides, or chemical molecules (e.g. drug candidates or fragments thereof). Typical analytes that can be used in the present invention include, but are not limited to, proteins and glycoproteins (e.g., antibodies or fragments thereof, affibodies, or aptamers), lipids, carbohydrates, enzymes, receptors, antigens, haptens, peptides, or chemical molecules (e.g. drug candidates or fragments thereof, specific or non-specific binders, chelators or aggregators). The term "antibody" describes an immunoglobulin whether natural or partly or wholly synthetically produced. The antibody may be monoclonal or polyclonal and may be prepared by techniques that are well-known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. The term "antibody" also covers any polypeptide or protein comprising an antibody antigen-binding site. Antibody fragments that comprise an antibody antigen-binding site include, but are not limited to molecules such as Fab, Fab', Fab'-SH, scFv, Fv, dAb, Fd; and diabodies.

Figure 1:
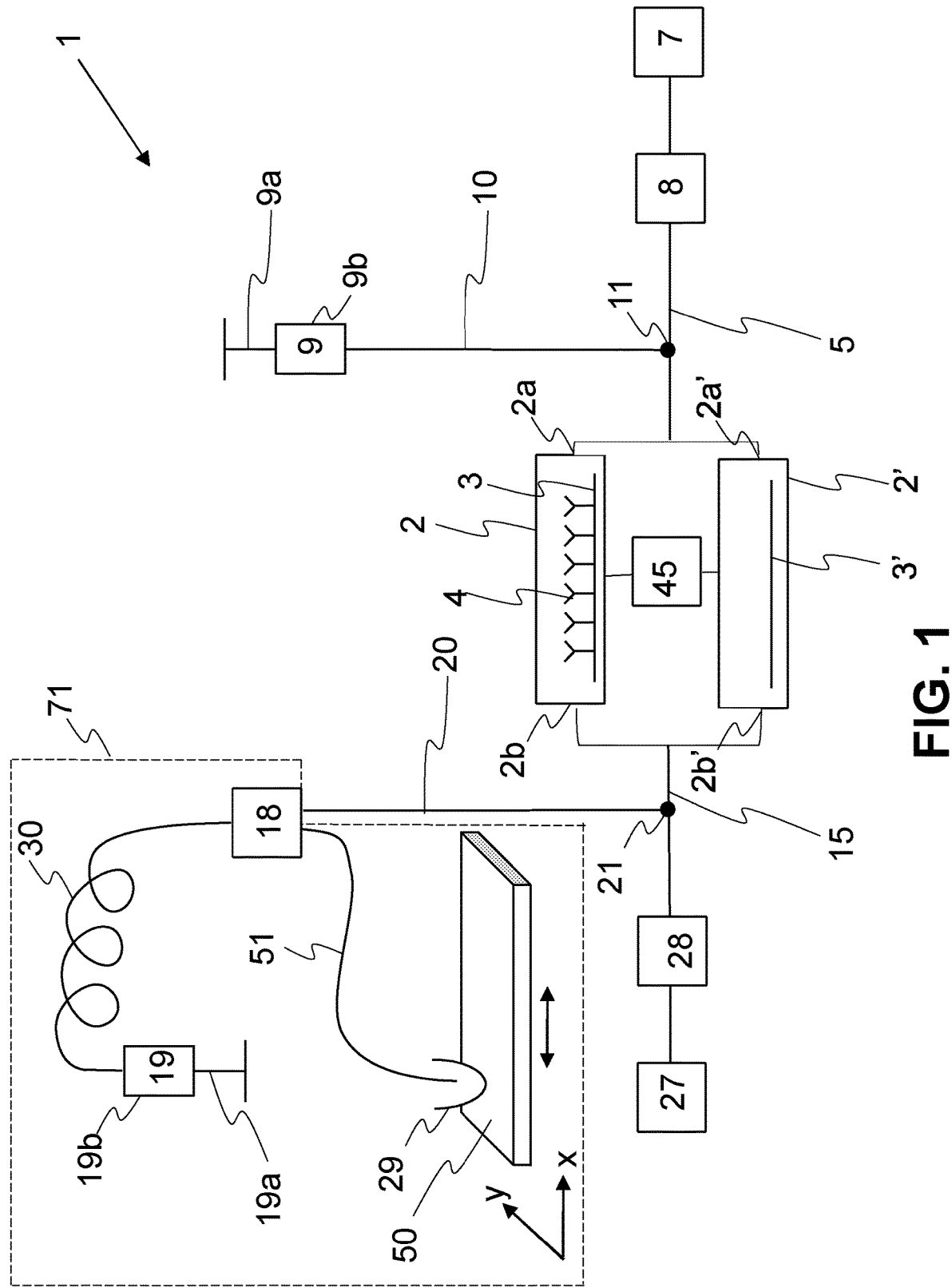
FIG. 1 provides a schematic view of a microfluidic assembly suitable for carrying out a methods according to the present invention.

FIG. 1 provides a schematic view of a microfluidic assembly 1 for carrying out the present invention. The microfluidic assembly 1 comprises a first flow cell 2 which comprises a first test surface 3 which comprises first ligands 4 and a second flow cell 2' which comprises a second test surface 3' which is without first ligands. It should be understood that in the present invention the second test surface 3' may be without any ligands, or, the second test surface 3' may have ligands but those ligands are not of the same type as the first ligands which are on the first test surface 3—in both cases the second test surface 3' would be without the first ligands. The first ligands 4 are preferably immobilized using amine coupling within a thin hydrogel layer such as a Dextran layer covalently bound to the first test surface 3; in another preferred embodiment the first ligands 4 are captured by a suitable tag such as hexahistidine or glutathione-S-transferase within a gel matrix such as Agarose within the first flow cell volume. Preferably, the first test surface 3 has an area of greater than 0.1 square millimetres, or greater than 0.5 square millimetres, or greater than 1 square millimetres, in order to increase the total amount of ligands for a given (predefined) ligand surface density (e.g. the density of the ligands on the first test surface 3 is a predefined density; thus increasing the area of the first test surface 3 and maintaining the density equal to the predefined density will increase the number of ligands in the first flow cell), which may be limited as an example by a hydrogel layer thickness and/or ligand size. The area may be the area of the flat surface, or including the inner surface of micropores present at the surface. Most preferably the area of the second test surface 3' is preferably equal to the area of the first test surface 3.

In the preferred embodiment the microfluidic assembly 1 furthermore comprises a sensor 45 (such as a Surface Plasmon Resonance sensor, or, Waveguide interferometry sensor, or, surface acoustic sensor) which is configured to measure changes on the first and second test surfaces 3,3' of the first and second flow cells 2,2'. Most preferably the sensor 45 is configured to measure binding taking place on each of the first and second test surfaces 3,3' (i.e. to measure binding of analyte in a sample fluid, to ligands on the first and second test surfaces 3,3'). Since the second test surface 3' is without ligands it can be expected that little or no binding will be measured by the sensor 45 for the second test surface 3'. The sensor 45 measures if analyte has become bound to the first ligands 4 within the first flow cell 2, and is preferably configured to measure the amount of analyte which is bound to the first ligands 4 within the first flow cell 2. Said sensor 45 is preferably operably connected to the first flow cell 2 and to the second flow cell 2', so that it can perform such measurements. The first ligands 4 can bind to analyte which has a predefined characteristic such as having a high affinity to the ligands 4 either via a simple lock-and-key mechanism where a molecule fits into a binding pocket of a ligand, or assisted by more complex molecular processes such as conformational changes. Thus it can be determined which analytes in a sample fluid have said predefined characteristic of having a high affinity to the ligands, by passing the sample fluid over the first test surface 3 of the first flow cell 2 and then determining which analytes have become bound to the first ligands 4.

The microfluidic assembly 1 further comprises a first conduit 5, one end of which is fluidly connected to a first fluidic port 2a of the first flow cell 2 and to a first fluidic port 2a' of the second flow cell 2', and the other end of which is fluidly connected to a first selection valve 8. The first selection valve 8 can selectively fluidly connect the first conduit 5 to a first waste reservoir 7. The first waste reservoir 7 can receive and store unwanted fluid such as cleaning effluent.

The first selection valve 8 is moveable between a first position and second position; when the first selection valve 8 is in its first position, the first selection valve 8 allows fluid to pass from first conduit 5 into the first waste reservoir 7; and when the first selection valve 8 is in its second position first selection valve 8 is closed thus preventing the flow of fluid out of the first conduit 5 via the first selection valve 8.

The microfluidic assembly 1 further comprises a first buffer reservoir 9 which contains a buffer fluid which can be used for cleaning parts of the microfluidic assembly 1. In this example first buffer reservoir 9 comprises a first syringe pump 9; the first syringe pump 9 comprises a receptacle 9b which contains buffer fluid, and a plunger 9a which can be selectively plunged into the receptacle 9b to release buffer fluid out of the first syringe pump 9. Additionally, moving the plunger in a direction out of receptacle 9b creates a negative pressure to aspirate buffer fluid into the first syringe pump 9. Preferably, the buffer fluid comprises a physiological buffer such as phosphate buffered saline solution (PBS) or HEPES buffered saline solution (HBS) with additives such as small fractions of detergents (for instance Polysorbate 20) and/or Dimethyl Sulfoxide (DMSO).

The first buffer reservoir 9 is fluidly connected to the first conduit 5 by means of a buffer conduit 10. The buffer conduit 10 connects with the first conduit 5 at a first junction 11. As illustrated in FIG. 1, in this example the buffer conduit 10 is arranged perpendicular to the first conduit 5 such that the first junction 11 is a T-shaped junction 11; however it will be understood that the first junction 11 may take any shape or configuration. Furthermore, the first junction 11 is a valveless junction (i.e. there are no valves present at the first junction 11). In a variation of this embodiment a valve is provided at the first junction 11; and the valve is moveable between a first open position and second closed position; in the first open position the valve is open to allow fluid flow between the buffer conduit 10 and the first conduit 5, and a second closed position the valve is closed block fluid flow between the buffer conduit 10 and the first conduit 5.

The microfluidic assembly 1 further comprises a second conduit 15 one end of which is fluidly connected to a second fluidic port 2b of the first flow cell 2 and to a second fluidic port 2b' of the second flow cell 2', and the other end of which is fluidly connected to a second selection valve 28; the second selection valve 28 can selectively fluidly connect the second conduit 5 to a second waste reservoir 27. The second waste reservoir 27 can receive and store unwanted fluid such as cleaning effluent.

Continuing with respect to the embodiment illustrated in FIG. 1, the second selection valve 28 is moveable between a first position and second position; when the second selection valve 28 is in its first position, the second selection valve 28 allows fluid to pass from the second conduit 15 into the second waste reservoir 27; and when the second selection valve 28 is in its second position the second selection valve 28 is closed thus preventing the flow of fluid out of the second conduit 15 into the second waste reservoir 27.

The microfluidic assembly 1 further comprises a second buffer reservoir 19 which contains a buffer fluid which can be used for cleaning parts of the microfluidic assembly 1. In this example second buffer reservoir 19 comprises a second syringe pump 19; the second syringe pump 19 comprises a receptacle 19b which contains buffer fluid, and a plunger 19a which can be selectively plunged into the receptacle 19b to selectively release buffer fluid out of the second syringe pump 19. Additionally, moving the plunger 19a in a direction out of receptacle 19b creates a negative pressure to aspirate buffer fluid into the second syringe pump 19. Preferably, the buffer fluid comprises a physiological buffer such as phosphate buffered saline solution (PBS).

The microfluidic assembly 1 further comprises a sample reservoir 29 which contains a sample fluid containing analyte which is to be tested for binding to the first ligands 4. The sample reservoir 29 is preferably a vial or a well of a microtiter plate. In this exemplary embodiment the sample reservoir 29 is located on an x-y table 50. The x-y table can be selectively moved (along the x or y axis—as illustrated by the double-headed arrows) so as to selectively bring either the sample reservoir 29 into fluid connection with an intermediate conduit 51. The intermediate conduit 51 is a hollow conduit with one open end adapted to aspirate liquid from the sample reservoir, preferably made from stainless steel or Polyetheretherketon (PEEK). The sample storage conduit can be a microfluidic tube made from PEEK or Polytetrafluorethylen (PTFE) or stainless steel, or a conduit within a layered manifold made from Polyimide.

FIG. 1 shows the x-y table in a position where the sample reservoir 29 is fluidly connected to intermediate conduit 51 whereby the x-y table 50 is positioned so that the sample reservoir 29 positioned under the free end of the intermediate conduit 51.

The microfluidic assembly 1 further comprises a third selection valve 18. The third selection valve 18 is fluidly connected to the intermediate conduit 51, thus the sample reservoir 29 can be selectively fluidly connected to the third selection valve 18. The third selection valve is further fluidly connected with the second syringe pump 19, via a storage conduit 30. In this example the storage conduit 30 is a coiled conduit so as to increase the volume of fluid which can be stored in the storage conduit 30. In this example the storage conduit 30 has an internal volume greater than 100 microliters. One end of the storage conduit 30 is fluidly connected to the second syringe pump 19 and the opposite end of the storage conduit 30 is fluidly connected to the third selection valve 18.

The storage conduit 30, x-y table 50, third selection valve 18, second buffer reservoir 19 (e.g. the second syringe pump 19), intermediate conduit 1, the sample reservoir 29, can be considered to collectively define a sample delivery unit 71.

In a variation of the embodiment, instead of the sample delivery unit 71 (i.e. instead of the group of components including the storage conduit 30, x-y table 50, second buffer reservoir 19, third selection valve 18, intermediate conduit 1 and the sample reservoir 29) any other suitable means for loading and storing sample fluid may be provided, such as an autosampler for example; for example autosampler model such as "Alias" made by Spark Holland, NL. could be provided in the assembly 1 instead of said above-mentioned group of components. Preferably in this variation of the embodiment the assembly will further comprise a pump which is operably connected to the autosampler.

Continuing with respect to the assembly illustrated in FIG. 1, the third selection valve 18 is fluidly connected to the second conduit 15 by means of a sample conduit 20. The sample conduit 20 connects with the second conduit 15 at a second junction 21. As illustrated in FIG. 1, in this example the sample conduit 20 is arranged perpendicular to the second conduit 15 such that the second junction 21 is a T-shaped junction 21; however it will be understood that the second junction 21 may take any shape or configuration. In this embodiment the second junction 21 is valveless (i.e. there is no valve present at the second junction 21). In a variation of this embodiment a valve is provided at the second junction 21; and the valve is moveable between a first open position and second closed position; in the first open position the valve is open to allow fluid flow between the sample conduit 20 and the second conduit 15, and a second closed position the valve is closed block fluid flow between the sample conduit 20 and the second conduit 15.

The third selection valve 18 is moveable between a first position and a second position. When the third selection valve 18 is in its first position the third selection valve 18 fluidly connects the intermediate conduit 51 with the storage conduit 30. Thus if the third selection valve 18 is in its first position, and the x-y table is positioned so that the intermediate conduit 51 is fluidly connected to the sample reservoir 29, then sample fluid in the sample reservoir can pass through conduit 51, and into the storage conduit 30 via the third selection valve 18.

When the third selection valve 18 is in its second position the third selection valve 18 fluidly connects the storage conduit 30 with the sample conduit 20; thus when the third selection valve 18 is in its second position fluid can flow from the storage conduit 30 into the sample conduit 20 via the third selection valve 18, or from the sample conduit 20 into the storage conduit 30 via the third selection valve 18.

The microfluidic assembly 1 can be used to implement an exemplary method according to a method embodiment of the present invention, as will be described in detail below:
Step (a)

Sample fluid which is to be tested, is provided in the sample reservoir 29 at a predetermined concentration $c_0$. Preferably, sample fluid comprises an analyte which is diluted in a buffer fluid to the predetermined concentration $c_0$. Preferably, the predetermined concentration $c_0$ is equal to or higher than a maximum expected equilibrium dissociation constant $K_{D,max}$ that should be measureable between the analyte and the ligands 4. For example, if a binding "hit" is to be detected in a primary drug candidate screening and a "hit" is defined as an analyte showing binding to first ligands 4 with an equilibrium dissociation constant $K_{D,max}$ below 100 μM, then the predetermined concentration $c_0$ is preferably chosen to be 100 μM or higher. It is known to the person skilled in the art that for determining kinetic rates of an interaction between analyte and ligand 4 using a series of injections of analyte at different concentrations, the highest analyte concentration should be approximately an order of magnitude higher than the maximum expected equilibrium dissociation constant $K_{D,max}$. Advantageously, in order to measure kinetic rates using the method of the present invention, the predetermined concentration $c_0$ of the analyte in the sample fluid does not need to be an order of magnitude higher than the maximum expected equilibrium dissociation constant $K_{D,max}$. Preferably, in the present invention the predetermined concentration $c_0$ of analyte in said sample fluid provided in the reservoir 29 (is $c_0=1 \times K_{D,max}$, or $c_0=2 \times K_{D,max}$, or $c_0=3 \times K_{D,max}$, wherein $K_{D,max}$ is the maximum expected equilibrium dissociation constant. The advantage of a lower concentration, such as $1 \times K_{D,max}$, is avoiding adverse effects such as bad analyte solubility, or analyte aggregation. The advantage of slightly higher concentration, such as $3 \times K_{D,max}$, is a lower error on evaluated kinetic rates for interactions with equilibrium dissociation constant close to $K_{D,max}$.

Most preferably all conduits, pumps, valves and the first flow cell 2 and second flow cell 2', of the microfluidic assembly 1 are rinsed, to evacuate remaining air and to clean the flow path from contaminants. To do this the third selection valve 18 is moved to its second position, and the first selection valve 8 is moved to its first position so the first selection valve 8 is open, and the second selection valve 28 is moved to its second position so the second selection valve 28 is closed. Then the plunger 19a is plunged into the receptacle 19b of the second syringe pump 19 so as to force more buffer fluid out of the second syringe pump 19. The buffer fluid which is released from the second syringe pump 19 pushes the buffer fluid into the storage conduit 30 and into the sample conduit 20, and then into the second conduit 15 and into the first flow cell 2 and second flow cell 2', and along the first conduit 5, and into the first waste reservoir 7 via the first selection valve 8. As it flows, the sample fluid also flushes out any air or contaminants present in the storage conduit 30, the sample conduit 20, the second conduit 15, the first flow cell 2, and the first conduit 5, into the first waste reservoir 7. Then, the first selection valve 8 is moved to its second position so the first selection valve 8 is closed, and the second selection valve 28 is moved to its first position so the second selection valve 28 is open. The plunger 9a is then plunged into the receptacle 9a so that buffer fluid is released from the first syringe pump 9. The buffer fluid flows out of the first syringe pump 9, through the buffer conduit 10, into the first conduit 5, and into the first flow cell 2 and second flow cell 2', and into the second conduit 15, and into the second waste reservoir 27.

At this point the sample conduit 20, the second conduit 15, the first flow cell 2 and the second flow cell 2', and the first conduit 5, and buffer conduit 10, are all filled with the buffer fluid.

The x-y table 50 is then moved so that the sample reservoir 29 is fluidly connected with the intermediate conduit 51. The third selection valve 18 is then moved to its first position so that the intermediate conduit 51 is fluidly connected with the storage conduit 30 via the third selection valve. With the third selection valve 18 in its first position, the plunger 19a of the second syringe pump 19 is moved in a direction out of receptacle 19b so as to create a negative pressure in the storage conduit 30. As a result a total pickup volume Vt of sample fluid is aspirated from the sample reservoir 29, into the intermediate conduit 51, and into the storage conduit 30 via the third selection valve 18. The total pickup volume Vt preferably is between 10 μL and 500 μL.

Next the third selection valve 18 is moved to its second position so that the third selection valve 18 fluidly connects the storage conduit 30 and the sample conduit 20. Optionally the plunger 19a is then plunged into the receptacle 19b of the second syringe pump 19 so as to force buffer fluid out of the second syringe pump 19. The buffer fluid which is released from the second syringe pump 19 pushes some of the sample fluid out of the storage conduit 30 and into the sample conduit 20. Since the first selection pump 8 is closed, pressure provided by buffer fluid which is present in the first flow cell 2 will prevent the sample fluid from flowing along the second conduit 15 towards the first and second flow cells 2,2'; furthermore since the second selection valve 28 is in its first position so that second selection valve 28 is open, the sample fluid will flow from the sample conduit 20 and into the second conduit 15 and into the second waste reservoir 27 via the second selection valve 28.

Preferably pressure provided by the buffer fluid present in the first flow cell 2 and second flow cell 2' prevents the sample fluid from flowing along the second conduit 15 into the first and second flow cells 2,2'. In some cases a negligible amount of sample fluid may move by diffusion along a portion of the second conduit 15 in direction of the first and second flow cell 2,2'. In order to prevent or at least minimize the diffusion of sample fluid along the second conduit 15 towards the first and second flow cell 2,2', preferably a flow of buffer fluid from the first buffer reservoir 9 through the first and second flow cell 2,2' and into the second waste reservoir 27 is maintained as the sample fluid is flowing from the storage conduit 30, along the sample conduit 20 and into the second waste reservoir 27.

Preferably, the volume of sample fluid which is allowed to flow from the storage conduit 30, along the sample conduit 20 and into the second waste reservoir 27, is more than twice the volume of the sample conduit 20, but is less than the total pickup volume Vt (i.e. less than the volume of sample fluid which was aspirated from the sample reservoir 29, into the intermediate conduit 51, and into the storage conduit 30 via the third selection valve 18). Thus there is some sample fluid remaining in the storage conduit 30.

Thus at this stage preferably the sample conduit 20 has been rinsed with the sample fluid; and is filled with sample fluid. At this stage preferably the buffer conduit 10, the first and second flow cell 2,2' all contain buffer fluid only; while preferably the sample conduit 20 contains sample fluid only.

Before the following steps are carried out and also during carrying of the following steps, the sensor 45 attached to the first and second flow cells 2, 2' is configured to output a binding curve for each of the first and second flow cells 2,2'. The binding curve output by the sensor 45 for the first flow cell 2, during this step (a), will be referred to hereafter as the single measurement binding curve; the single measurement binding curve will is a signal which represents the amount of analyte bound to the ligands 4 on the first test surface 3 of the first flow cell 2, over time). The binding curve output by the sensor 45 for the second flow cell 2', during this step (a), will be referred to hereafter as the single reference binding curve. It should be noted that since the second test surface 3' of the second flow cell 2' is without ligands, one can expect that the single reference binding curve would be a constant 'zero' indicating no binding; however in practice this is not the case; in practice due to refractive index contributions, the single reference binding curve will be non-zero.

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a first volume $V_1$ of buffer fluid out of the second syringe pump 19, wherein the first volume $V_1$ is smaller than the total pickup volume Vt. The buffer fluid which is released from the second syringe pump 19 pushes a corresponding first volume $V_1$ of the sample fluid out of the storage conduit 30 and into the sample conduit 20. Since the first selection valve 8 is in its second position (i.e. the first selection valve 8 is open) the buffer fluid present in the first and second flow cells 2,2' no longer provides a pressure which prevents the sample fluid from flowing along the second conduit 15 into the first and second flow cells 2,2'. Accordingly, the sample fluid which is now passing into the sample conduit 20 flows into the second conduit 15, flows simultaneously into the first and second flow cells 2,2' at a time $t_{s0}$, and along the first conduit 5, and into the first waste reservoir 7 via the first selection valve 8. As it flows, the sample fluid also at least partially flushes out buffer fluid present in the first and second flow cells 2,2', and the first conduit 5, into the first waste reservoir 7 (preferably the sample fluid flushes out all the buffer fluid present in the first and second flow cells 2,2', and the first conduit, and in the portion of the second conduit 15 between the second junction 21 and the first flow cell 3, into the first waste reservoir 7).

Thus, at this stage the sample conduit 20, the portion of the second conduit 15 between the second junction 21 and the first and second flow cells 2,2', and the first conduit 5 all contain sample fluid only. Advantageously, since prior to moving the first selection valve 8 to its second position there is sample fluid already present in the sample conduit 20, this allows the concentration of sample fluid within the first and second flow cells 2,2' to increase quickly when the first selection valve 8 is moved to its second position.

The first analyte duration $t_{1a}$ is the duration of time the first volume V1 of sample fluid flows over the first and second test surfaces 3,3' of the first and second flow cells 2,2'. Thus, the first analyte duration $t_1$ is equal to the duration of time the first volume V1 of sample fluid is injected into the first and second flow cells 2,2' (as described in steps outlined in the preceding paragraph); and more specifically, in one example, referring to the steps described in the preceding paragraphs, the first analyte duration $t_1$ can be defined as the time duration between starting to plunge the plunger 19a into the receptacle 19b of the second syringe pump 19 to eject said first volume V1 of buffer fluid from the syringe pump and stopping to plunge the plunger 19a into the receptacle 19b of the second syringe pump 19. The average flowrate $f_{1a}$ at which the first sample fluid volume is injected corresponds to $V_1/t_{1a}$. Preferably, $t_1$ is between 10 milliseconds and 60 minutes, and $f_1$ is between 1 μL/min and 1 mL/min, and $V_1$ is between 0.1 μL and 200 μL.

Next the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19a is fixed so as to prevent the flow of fluid into or out of the receptacle 19b of the second syringe pump 19. The plunger 9a of the first syringe pump 9 is then plunged into the receptacle 9b so that a first volume $V_1'$ of buffer fluid (which is free from analyte) is released from the first syringe pump 9. The buffer fluid released from the first syringe pump 9 will flow through the first conduit 5, simultaneously into first and second flow cells 2,2' at a time $t_{b0}$, and into the second conduit 15 and into the second waste reservoir 27. As it flows, the buffer fluid also at least partially flushes out sample fluid present in the first and second flow cells 2,2', and the second conduit 15, and the portion of the first conduit between first junction 11 and the flow cell 2, into the second waste reservoir 27 (preferably the buffer fluid partially flushes out all the sample fluid present in the first and second flow cells 2,2', and the second conduit 15, and the portion of the first conduit between first junction 11 and the first and second flow cells 2,2', into the second waste reservoir 27). When the buffer fluid passes over the first test surface 3 of the first flow cell 2, analyte which was belonging to the first volume V1 of sample fluid and which was previously bound with the first ligands 4 but which has passively dissociated from first ligands 4 is flushed into the second waste reservoir 27. Furthermore in the preferred embodiment the first volume $V_1'$ of buffer fluid is configured (i.e. has a composition) to cause analyte (which was belonging to the first volume V1 of sample fluid) which is bound to the first ligands 4 to dissociate from the first ligands 4; the analyte which is dissociated from the first ligands 4 by the buffer is flushed through the first flow cell 2, the second conduit 15 and into the second waste reservoir 27.

The first buffer duration $t_{1b}$ is how long the first volume $V_1'$ of buffer fluid is injected from the first syringe pump 9 into the first and second flow cells 2,2' in above step, and defined as the difference in time between starting to plunge the plunger 9a of the first syringe pump 9 into the receptacle 9b so as to eject the first volume $V_1'$ of buffer fluid from the first syringe pump 9, and stopping to plunge the plunger 9a into the receptacle 9b. The average flowrate $f_{1b}$ at which the first volume $V_1'$ of buffer fluid is injected corresponds to $V_1'/t_{1b}$. Preferably, $t_{1b}$ is between 10 milliseconds and 60 minutes, and $f_1'$ is between 0.1 µL/min and 1 ml/min, and $V_1'$ is between 1 µL and 200 µL.

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a second volume $V_2$ of buffer fluid out of the second syringe pump 19, wherein the second volume $V_2$ is smaller than the total pickup volume Vt. The second volume $V_2$ of buffer fluid which is released from the second syringe pump 19 pushes a corresponding second volume $V_2$ of the sample fluid remaining in the storage conduit 30, out of the storage conduit 30 and into the sample conduit 20. In the preferred embodiment the second volume $V_2$ of sample fluid is larger than the first volume of sample fluid $V_1$. Since the first selection valve 8 is in its second position (i.e. the first selection valve 8 is open) the buffer fluid present in the first flow cell 2 no longer provides a pressure which prevents the sample fluid from flowing along the second conduit 15 into the first and second flow cells 2,2'. Accordingly the sample fluid which is now passing into the sample conduit 20 flows into the second conduit 15, and flows simultaneously into the first and second flow cells 2,2' at a time $t_{s1}$, and along the first conduit 5, and into the first waste reservoir 7 via the first selection valve 8. As it flows, the sample fluid also at least partially flushes out buffer fluid present in the first and second flow cells 2,2', and the first conduit 5, into the first waste reservoir 7. When the sample fluid passes over the first test surface 3 of the first flow cell 2, analyte contained in the sample fluid which has a predefined characteristic necessary to allow them to bind with the first ligands 4 on the surface, will bind with the first ligands 4.

The second analyte duration $t_{2a}$ is the duration of time the second volume V2 of sample fluid flows over the first and second test surfaces 3,3' of the first and second flow cells 2,2'. Thus, the second analyte duration $t_{2a}$ is equal to the duration of time the second volume V2 of sample fluid is injected into the first and second flow cells 2,2', (as described in steps outlined in the preceding paragraphs); more specifically, in one example, referring to the steps described in the preceding paragraphs, the second analyte duration $t_2$ can be defined as the difference in time between starting to plunge the plunger 19a into the receptacle 19b of the second syringe pump 19 to eject said second volume $V_2$ of buffer from the syringe pump, and stopping to plunge the plunger 19a into the receptacle 19b of the second syringe pump 19. The average flowrate $f_{2a}$ at which the second volume $V_2$ of sample fluid (containing the analyte) is injected corresponds to $V_2/t_{2a}$. Preferably, $t_2$ is between 10 milliseconds and 60 minutes, and $f_{2a}$ is between 1 µL/min and 1 mL/min, and $V_1$ is between 0.1 µL and 200 µL.

Importantly in the present invention the first analyte duration $t_{1a}$ is shorter than the second analyte duration $t_{2a}$. Importantly, the predetermined concentration $c_0$ of analyte in the first volume V1 of sample fluid is the same as the predetermined concentration $c_0$ of the analyte in the second volume V2 of sample fluid.

It should be understood that other volumes of sample fluid can be injected into the flow cell before the first volume V1 of sample fluid, and/or between injecting the first volume V1 of sample fluid and the second volume V2 of sample fluid; in other words the above mentioned first volume V1 of sample fluid and second volume V2 of sample fluid do not necessarily need to be consecutive to one another; neither do they need to constitute the first and second volumes injected in a sequence of sample fluid volume injections, rather they can occur at any point in the sequence and may occur in any order.

Advantageously, in the present invention, the sample conduit 20 does not need to be rinsed (with buffer for example or any other suitable rinsing material) between flowing the first volume V1 of sample fluid through the sample conduit 20 and over the first test surface 3, and flowing the second volume V2 of sample fluid through the sample conduit 20 and over the first test surface 3.

Next, preferably, the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19a is fixed so as to prevent the flow of fluid into or out of the receptacle 19b of the second syringe pump 19. The plunger 9a of the first syringe pump 9 is then plunged into the receptacle 9b so that a second volume of buffer fluid $V_2'$ is ejected from the first syringe pump 9. The second volume of buffer fluid $V_2'$ released from the first syringe pump 9 will flow through the first conduit 5, and simultaneously through the first and second flow cells 2,2' at a $t_{b1}$, along the second conduit 15 and into the second waste reservoir 27. As it flows, the buffer fluid will also at least partially flush out sample fluid present in the first and second flow cells 2,2', and the second conduit 15, and in the portion of the first conduit 5 between the first junction 11 and the flow cell, into the second waste reservoir 27. (preferably the buffer fluid flushes out all the sample fluid present in the first and second flow cells 2,2', and the second conduit 15, and the portion of the first conduit 5 between first junction 11 and the first and second flow cells 2,2', into the second waste reservoir 27). When the second volume of buffer fluid $V_2'$ passes over the first test surface 3 of the first flow cell 2, analyte which was belonging to the second volume V2 of sample fluid and which was previously bound with first ligands 4 but which has passively dissociated from first ligands 4) is flushed into the second waste reservoir 27. Furthermore in the preferred embodiment the second volume $V_2'$ of buffer fluid is configured (i.e. has a suitable composition) to cause analyte (which was belonging to the second volume V2 of sample fluid) which is bound with the first ligands 4 to dissociate from those first ligands 4; the analyte which is dissociated from the first ligands 4 by the buffer is flushed through the first flow cell 2, the second conduit 15 and into the second waste reservoir 27.

The second buffer duration $t_{2b}$ is how long the second volume $V_2'$ of buffer fluid is injected from the first syringe pump 9 into the first and second flow cells 2,2' in above step, and defined as the difference in time between starting to plunge the plunger 9a of the first syringe pump 9 into the receptacle 9b so as to eject the second volume $V_2'$ of buffer fluid from the first syringe pump 9, and stopping to plunge the plunger 9a into the receptacle 9b. The average flowrate $f_{2b}'$ at which the first fluid volume free from analyte is injected corresponds to $V_2'/t_{2b}'$. Preferably, $t_2'$ is between 10 milliseconds and 60 minutes, and $f_{2b}'$ is between 0.1 μL/min and 1 ml/min, and $V_2'$ is between 1 μL and 200 μL.

As mentioned the sensor measures the binding on the first and second test surfaces 3,3' of the respective first and second flow cells 2,2' as the first and second volumes of sample fluid (V1, V2) and first and second volumes of buffer fluid (V1',V2') are flowed through the first and second flow cells 2,2'; the sensor 45 outputs a the single measurement binding curve and a single reference binding curve.

When the first and second volumes $V_1$ $V_2$ of the sample fluid pass over the first test surface 3 of the first flow cell 2, analyte contained in the first and second volumes $V_1$ $V_2$ of the sample fluid which has a predefined characteristic necessary to allow them to bind with the first ligands 4 on the first test surface 3, will bind with the first ligands 4; this binding will be indicated in the single measurement binding curve output by the sensor 45. The sensor also measures binding at the first test surface 3 of the first flow cell 2 as the first and second volumes $V_1',V_2'$ of buffer fluid are passed over the first test surface 3 of the first flow cell 2; in the preferred embodiment the first and second volumes $V_1',V_2'$ of buffer fluid are configured to cause analyte, which is bound to the ligands 4 on the first test surface 3, to dissociate from the ligands 4; this reduction in binding will be indicated in the single measurement binding curve output by the sensor 45.

The second test surface 3' is without ligands and therefore the single reference binding curve will not indicate any binding; however the single reference binding curve is non-zero; any activity which is indicated in the a single reference binding curve will be due to refractive index effects caused by the first and second volumes $V_1$ $V_2$ of the sample fluid and the first and second volumes $V_1',V_2'$ of buffer fluid as they flow through the second flow cell 2'. When the first and second volumes $V_1$ $V_2$ of the sample fluid pass over the second test surface 3' of the second flow cell 2', refractive index caused by first and second volumes $V_1$ $V_2$ of the sample fluid will cause the single reference binding curve to be non-zero; the refractive index contributions of the first and second volumes $V_1$ $V_2$ of the sample fluid will be indicated in the single reference binding curve output by the sensor 45. When the first and second volumes $V_1',V_2'$ of buffer fluid pass over the second test surface 3' of the second flow cell 2', refractive index caused by first and second volumes $V_1',V_2'$ of buffer fluid will cause the single reference binding curve to be non-zero; the refractive index contributions of the first and second volumes $V_1',V_2'$ of buffer fluid will be indicated in the single reference binding curve output by the sensor 45.

It is understood that the single measurement binding curve and/or the single reference binding curve which are output by the sensor 45 in this step (a) can be divided into segments for processing.

The above-mentioned steps described in this step (a) may be repeated a plurality of times so that a corresponding plurality of volumes of sample fluid are passed through the first and second flow cells 2,2'. In the preferred embodiment, the steps of injecting sample fluid volumes (which contains analyte) and injecting buffer fluid volumes (which are free from analyte) are then repeated a plurality of times so that a plurality of volumes of sample fluid are passed through the first and second flow cells 2,2'; preferably these steps are repeated three times or four times or five times or six times or seven times or eight times or nine times or ten times. The advantage of repeating the steps of injecting sample fluid volumes (each containing analyte) and injecting buffer fluid volumes (which are free from analyte) a low number of times (e.g. repeating three times) are that the total duration of the experiment is reduced. This is especially suitable for weak binders, such as having an affinity in the uM or mM range, encountered in early stage drug candidate screening. The advantage of repeating the steps of injecting sample fluid volumes (containing the analyte) and injecting buffer fluid volumes (which are free from analyte) are larger number of times (such as between five to ten times) are that the a greater range of kinetic parameters can be determined, or that the kinetic parameters can be determined with greater accuracy. This is especially suitable for tighter binders, such as with an affinity in the nM or pM range.

Figure 2:
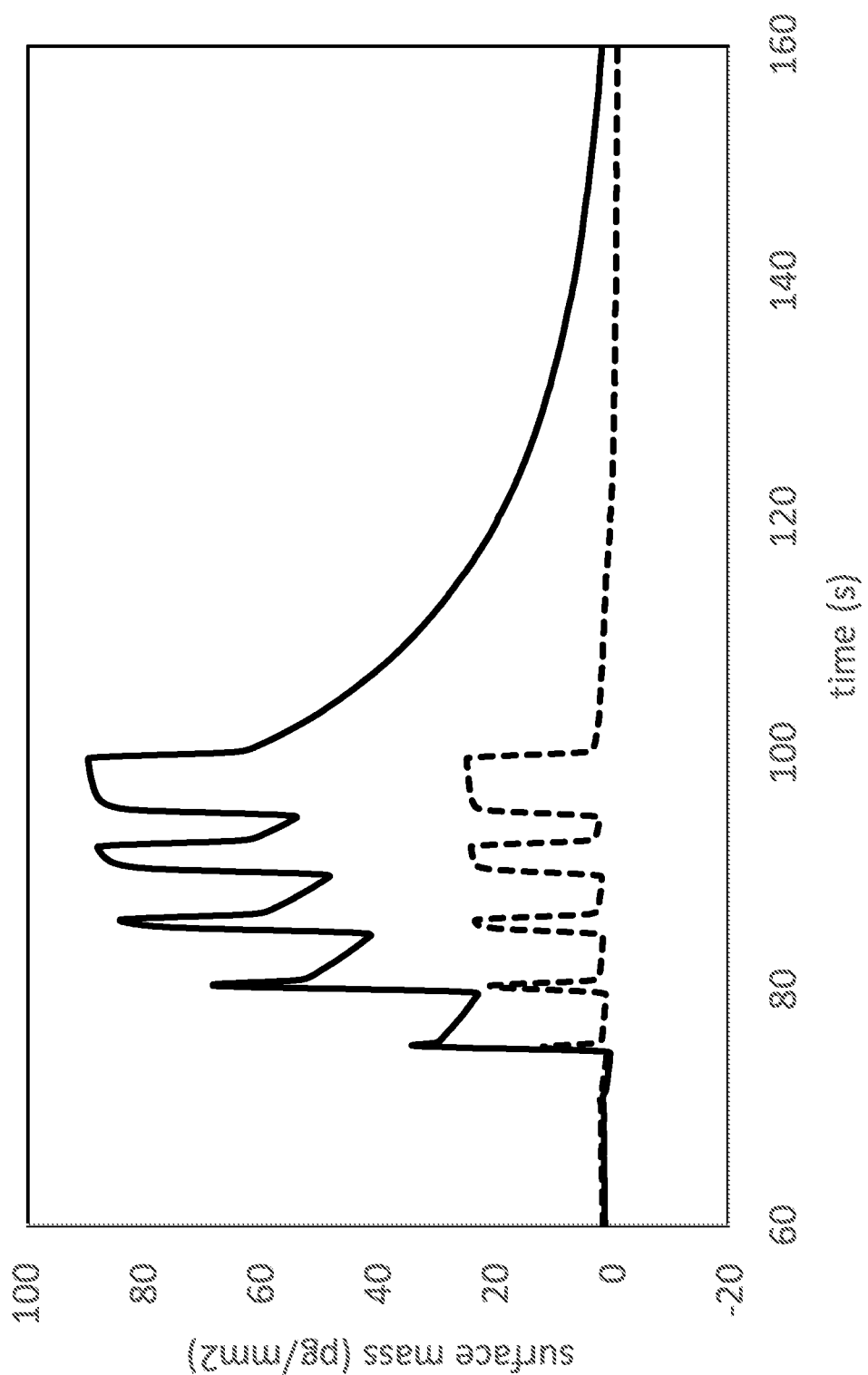
FIG. 2 shows an example of a single measurement binding curve and a single reference binding curve which are output by the sensor of the assembly of FIG. 1 when performing a method according to the present invention.

As example FIG. 2 shows an example of single measurement binding curve (continuous line) and the single reference binding curve (dashed line) output from the sensor 45, for an exemplary embodiment wherein the afore-mentioned steps (i.e. the injecting a sample fluid volume (containing the analyte) and injecting buffer fluid volume (which is free from analyte) have been carried out '5' times (i.e. '5' sample fluid volumes and '5' buffer fluid volumes have been flowed through the first and second flow cells 2,2'). The x-axis of the graph denotes time in seconds, and the y-axis denotes surface mass in pg/mm2.

In the depicted example, the analyte comprised in each of the sample volumes, and which can bind to the ligands 4 in the flow cell, is Furosemide (Sigma-Aldrich product number F4381) at a predetermined concentration $c_o$ of 100 uM. In other words each of the sample fluid volumes comprises Furosemide at a predetermined concentration $c_o$ of 100 uM; the buffer fluid volumes were without analyte i.e. the buffer fluid volumes did not contain any Furosemide. The first volume of the sample fluid V1 was injected at x=75 s, with a first analyte duration $t_{1a}$ of 312.5 ms, followed by a first volume of buffer fluid V1' with a first buffer duration $t_{1b}$ of 4.6875 s, followed by the second volume of the sample fluid V2 with a second analyte duration $t_{2a}$ of 625 ms, followed by a second volume of buffer fluid V2' with a second buffer duration $t_{2b}$ of 4.375 s, followed by a third volume of the sample fluid V3 with a third analyte duration $t_{3a}$ of 1.25 s, followed by a third volume of buffer fluid V3' with a third buffer duration $t_{3b}$ of 3.75 s, followed by a fourth volume of the sample fluid V4 with a fourth analyte duration $t_{4a}$ of 2.5 s, followed by a fourth volume of buffer fluid V4' with a fourth buffer duration $t_{4b}$ of 2.5 s, followed by a fifth volume of the sample fluid V5 with a fifth analyte duration $t_{5a}$ of 5 s, followed by a fifth volume of buffer fluid V5' with a fifth buffer duration $t_{5b}$ of 200 s (not all data shown). Throughout the measurement, the flowrate for the sample fluid volumes and the buffer fluid volumes were 80 ul/min.

It should be noted that sensor 45 make take any suitable form. A Creoptix WAVEdelta system operated at an acquisition frequency of 10 Hz and 25° C. flow cell temperature, and a disposable sensor chip (such as for example "WAVEchip 4PCH" from Creoptix AG) comprising the first flow cell 2 (which comprises ligands 4 on its first test surface 3) and the second flow cell 2'(whose second test surface 3' is without ligands), was used to obtain the single measurement binding curve and the single reference binding curve shown in FIG. 2. The Creoptix WAVEdelta system was modified in its measurement processes to allow multiple injections from a single sample reservoir. Prior to obtaining the depicted measurement in FIG. 2, Carbonic Anhydrase Isozyme II from bovine erythrocytes ("CAII", Sigma-Aldrich product Nr. C2522) was immobilized (at a density of ~10,400 pg/mm2) as ligands 4 onto a PCH WAVEchip on the first test surface 3 of the first flow cell 2 using amine coupling. The second test surface 3 of the second flow cell 2' was left empty, without ligands. PBS buffer pH 7.43% DMSO was used as buffer i.e. each of the volumes of buffer fluid V1'-V5' comprise PBS buffer pH 7.43% DMSO.

Step (b)

After, or before, the above step (a) or below step (c) have been performed, volumes of sample buffer fluid are respectively passed through the first and second flow cells 2,2', and the sensor 45 outputs a binding curve for each respective flow cell 2,2' as these sample buffer fluid volumes are respectively passed through the first and second flow cells 2,2'. The volumes of sample buffer fluid are passed through the first and second flow cells at the same rate, interval, flow rate, and duration of time, as the volumes of sample fluid (V1, V2) in step (a); for example in this example two volumes of sample fluid V1,V2 were passed through the first and second flow cells 2,2' so two volumes of sample buffer fluid will be passed through the flow cells in this step (b); the interval between injecting the two volumes of sample buffer fluid into the first and second flow cells 2,2' will be equal to the interval between the injecting two volumes of sample fluid V1,V2 (i.e. equal to the interval between $t_{s0}$ and $t_{s1}$); also the flow rate and period to inject the two volumes of sample buffer fluid will be the same as the two volumes of sample fluid V1,V2 in step (a). The binding curve which the sensor 45 outputs for the first flow cell 2, as these sample buffer fluid volumes are respectively passed through the first flow cell 2, is referred to as the single blank measurement binding curve; and the binding curve which the sensor 45 outputs for the second flow cell as these sample buffer fluid volumes are respectively passed through the second flow cell 2', is referred to as the single blank reference binding curve. This step (b) will now, be described in more detail:

Sample buffer fluid is provided in the sample reservoir 29. It should be understood that the sample buffer fluid which is provided it the sample reservoir 29 may be the same as, or different to, the buffer fluid provided in the first syringe pump 9 and/or may be the same as, or different to, the buffer fluid provided in the second syringe pump 19.

Most preferably all conduits, pumps, valves and the first flow cell 2 and second flow cell 2', of the microfluidic assembly 1 are rinsed, to evacuate remaining air and to clean the flow path from contaminants. To do this the third selection valve 18 is moved to its second position, and the first selection valve 8 is moved to its first position so the first selection valve 8 is open, and the second selection valve 28 is moved to its second position so the second selection valve 28 is closed. Then the plunger 19a is plunged into the receptacle 19b of the second syringe pump 19 so as to force more buffer fluid out of the second syringe pump 19. The buffer fluid which is released from the second syringe pump 19 pushes the buffer fluid into the storage conduit 30 and into the sample conduit 20, and then into the second conduit 15 and into the first flow cell 2 and second flow cell 2', and along the first conduit 5, and into the first waste reservoir 7 via the first selection valve 8. As it flows, the buffer fluid also flushes out any air or contaminants present in the storage conduit 30, the sample conduit 20, the second conduit 15, the first flow cell 2, and the first conduit 5, into the first waste reservoir 7. Then, the first selection valve 8 is moved to its second position so the first selection valve 8 is closed, and the second selection valve 28 is moved to its first position so the second selection valve 28 is open. The plunger 9a is then plunged into the receptacle 9a so that buffer fluid is released from the first syringe pump 9. The buffer fluid flows out of the first syringe pump 9, through the buffer conduit 10, into the first conduit 5, and into the first flow cell 2 and second flow cell 2', and into the second conduit 15, and into the second waste reservoir 27.

At this point the sample conduit 20, the second conduit 15, the first flow cell 2 and the second flow cell 2', and the first conduit 5, and buffer conduit 10, are all filled with the buffer fluid.

The x-y table 50 is then moved so that the sample reservoir 29 is fluidly connected with the intermediate conduit 51. The third selection valve 18 is then moved to its first position so that the intermediate conduit 51 is fluidly connected with the storage conduit 30 via the third selection valve. With the third selection valve 18 in its first position, the plunger 19a of the second syringe pump 19 is moved in a direction out of receptacle 19b so as to create a negative pressure in the storage conduit 30. As a result a total pickup volume VBt of sample buffer fluid is aspirated from the sample reservoir 29, into the intermediate conduit 51, and into the storage conduit 30 via the third selection valve 18.

Next the third selection valve 18 is moved to its second position so that the third selection valve 18 fluidly connects the storage conduit 30 and the sample conduit 20. Optionally the plunger 19a is then plunged into the receptacle 19b of the second syringe pump 19 so as to force buffer fluid out of the second syringe pump 19. The buffer fluid which is released from the second syringe pump 19 pushes some of the sample buffer fluid out of the storage conduit 30 and into the sample conduit 20. Since the first selection pump 8 is closed, pressure provided by buffer fluid which is present in the first flow cell 2 will prevent the sample buffer fluid from flowing along the second conduit 15 towards the first and second flow cells 2,2'; furthermore since the second selection valve 28 is in its first position so that second selection valve 28 is open, the sample buffer fluid will flow from the sample conduit 20 and into the second conduit 15 and into the second waste reservoir 27 via the second selection valve 28.

Preferably pressure provided by the buffer fluid present in the first flow cell 2 and second flow cell 2' prevents the sample buffer fluid from flowing along the second conduit 15 into the first and second flow cells 2,2'. In some cases a negligible amount of sample buffer fluid may move by diffusion along a portion of the second conduit 15 in direction of the first and second flow cell 2,2'. In order to prevent or at least minimize the diffusion of sample buffer fluid along the second conduit 15 towards the first and second flow cell 2,2', preferably a flow of buffer fluid from the first buffer reservoir 9 through the first and second flow cell 2,2' and into the second waste reservoir 27 is maintained as the sample buffer fluid is flowing from the storage conduit 30, along the sample conduit 20 and into the second waste reservoir 27.

Preferably, the volume of sample buffer fluid which is allowed to flow from the storage conduit 30, along the sample conduit 20 and into the second waste reservoir 27, is more than twice the volume of the sample conduit 20, but is less than the total pickup volume VBt (i.e. less than the volume of sample buffer fluid which was aspirated from the sample reservoir 29, into the intermediate conduit 51, and into the storage conduit 30 via the third selection valve 18). Thus there is some sample buffer fluid remaining in the storage conduit 30.

Thus at this stage preferably the sample conduit 20 has been rinsed with the sample buffer fluid; and is filled with sample buffer fluid. At this stage preferably the buffer conduit 10, the first and second flow cell 2,2' all contain buffer fluid only; while preferably the sample conduit 20 contains sample buffer fluid.

Before the following steps are carried out and also during carrying of the following steps, the sensor 45 attached to the first and second flow cells 2, 2' is configured to output a binding curve for each of the first and second flow cells 2,2'. The binding curve output by the sensor 45 for the first flow cell 2, during this step (b), will be referred to hereafter as the single blank measurement binding curve. The binding curve output by the sensor 45 for the second flow cell 2', during this step (b), will be referred to hereafter as the single blank reference binding curve. The sample buffer fluid which was provided in the sample reservoir 29 does not comprise any analyte which could bind to the ligands 4 on the first test surface 3 of the first flow cell 2; moreover the second test surface 3' of the second flow cell 2' does not comprise ligands. Accordingly, one would expect that the single blank measurement binding curve and the single blank reference binding curve will each be a constant 'zero' as no binding can take place on the first and second test surfaces 3,3' as the sample buffer fluid is flowed over the first and second test surfaces 3,3' of the respective first and second flow cells 2,2'. However, in practice at least one of the single blank measurement binding curve and/or the single blank reference binding curve will comprise non-zero values; and the single blank measurement binding curve and the single blank reference binding curve will differ from one another, due to systematic errors.

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a first volume $V_{1B}$ of buffer fluid out of the second syringe pump 19, wherein the first volume $V_{1B}$ is smaller than the total pickup volume VBt. The buffer fluid which is released from the second syringe pump 19 pushes a corresponding first volume $V_{1B}$ of the sample buffer fluid out of the storage conduit 30 and into the sample conduit 20.

The sample buffer fluid which is now passing into the sample conduit 20 flows into the second conduit 15, flows simultaneously into the first and second flow cells 2,2' at a time $t_{B0}$, and along the first conduit 5, and into the first waste reservoir 7 via the first selection valve 8. As it flows, the sample buffer fluid also at least partially flushes out buffer fluid present in the first and second flow cells 2,2', and the first conduit 5, into the first waste reservoir 7 (preferably the sample buffer fluid flushes out all the buffer fluid present in the first and second flow cells 2,2', and the first conduit, and in the portion of the second conduit 15 between the second junction 21 and the first flow cell 3, into the first waste reservoir 7).

Thus, at this stage the sample conduit 20, the portion of the second conduit 15 between the second junction 21 and the first and second flow cells 2,2', and the first conduit 5 all contain sample buffer fluid only.

The first volume $V_{1B}$ of sample buffer fluid is equal to the first volume V1 of sample fluid in step (a).

The duration of time ($t_{1B}$) the first volume $V_{1B}$ of sample buffer fluid flows over the first and second test surfaces 3,3' of the first and second flow cells 2,2' is equal to the first analyte duration $t_{1a}$ in step (a).

The average flowrate ($V_{1B}/t_{1B}$) at which the first volume $V_{1B}$ of sample buffer fluid is injected is equal to the to the average flowrate of the first sample volume $f_{1a}$ in step (a).

Next the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19a is fixed so as to prevent the flow of fluid into or out of the receptacle 19b of the second syringe pump 19. The plunger 9a of the first syringe pump 9 is then plunged into the receptacle 9b so that a first volume $V_1'$ of buffer fluid is released from the first syringe pump 9. The first volume $V_1'$ of buffer fluid is equal to the first volume $V_1'$ of buffer fluid in step (a). The buffer fluid released from the first syringe pump 9 will flow through the first conduit 5, simultaneously into first and second flow cells 2,2' at a time $t_{Bb0}$, and into the second conduit 15 and into the second waste reservoir 27. As it flows, the buffer fluid (from the first syringe pump 9) also at least partially flushes out buffer fluid (originally from the sample reservoir 29) present in the first and second flow cells 2,2', and the second conduit 15, and the portion of the first conduit between first junction 11 and the flow cell 2, into the second waste reservoir 27 (preferably the buffer fluid flushes out all the buffer fluid (originally from the sample reservoir 29) present in the first and second flow cells 2,2', and the second conduit 15, and the portion of the first conduit between first junction 11 and the first and second flow cells 2,2', into the second waste reservoir 27).

The first buffer duration $t_{1b}$ is a measure of how long the first volume $V_1'$ of buffer fluid is injected from the first syringe pump 9 into the first and second flow cells 2,2'; the first buffer duration $t_{1b}$ in this step (b) is equal to the first buffer duration $t_{1b}$ in step (a).

The average flowrate ($V_1'/t_{1b}$) at which the first volume $V_1'$ of buffer fluid is injected in this step (b) is equal to the average flowrate $f_{1b}'$ at which the first volume $V_1'$ of buffer fluid is injected in step (a).

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a second volume $V_{2B}$ of buffer fluid out of the second syringe pump 19, wherein the second volume $V_{2B}$ of buffer fluid is smaller than the total pickup volume VBt. The second volume $V_{2B}$ of buffer fluid which is released from the second syringe pump 19 pushes a corresponding second volume $V_{2B}$ of sample buffer fluid remaining in the storage conduit 30, out of the storage conduit 30 and into the sample conduit 20.

Since the first selection valve 8 is in its second position (i.e. the first selection valve 8 is open) the buffer fluid present in the first flow cell 2 no longer provides a pressure which prevents the sample buffer fluid from flowing along the second conduit 15 into the first and second flow cells 2,2'. Accordingly the second volume $V_{2B}$ of sample buffer fluid which is now passing into the sample conduit 20 flows into the second conduit 15, and flows simultaneously into the first and second flow cells 2,2' at a time $t_{B1}$, and along the first conduit 5, and into the first waste reservoir 7 via the first selection valve 8. As it flows, the second volume $V_{2B}$ of sample buffer fluid also at least partially flushes out buffer fluid present in the first and second flow cells 2,2', and the first conduit 5, into the first waste reservoir 7.

The duration of time interval between $t_{B0}$ (the time which the first volume $V_{1B}$ of the sample buffer fluid begins to flow over the first and second test surfaces 3,3') and $t_{B1}$ (the time which the second volume $V_{2B}$ of the sample buffer fluid begins to flow over the first and second test surfaces 3,3') in this step (b), is equal to the time interval between $t_{s0}$ (the time which the first volume V1 of the sample fluid begins to flow over the first and second test surfaces 3,3') and $t_{s1}$ (the time which the second volume V2 of the sample fluid begins to flow over the first and second test surfaces 3,3') in step (a).

The second volume $V_{2B}$ of sample buffer fluid in this step (b) is equal to the second volume V2 of sample fluid in step (a).

The duration of time ($t_{2B}$) the second volume $V_{2B}$ of sample buffer fluid flows over the first and second test surfaces 3,3' of the first and second flow cells 2,2' is equal to the second analyte duration $t_{2a}$ in step (a).

The average flowrate ($V_{2B}/t_{2B}$) at which the second volume $V_{2s}$ of sample buffer fluid volume is injected is equal to the to the average flowrate of the second sample volume $f_{2a}$ in step (a).

Next, preferably, the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19a is fixed so as to prevent the flow of fluid into or out of the receptacle 19b of the second syringe pump 19. The plunger 9a of the first syringe pump 9 is then plunged into the receptacle 9b so that a second volume of buffer fluid $V_2'$ is ejected from the first syringe pump 9. The second volume of buffer fluid $V_2'$ released from the first syringe pump 9 will flow through the first conduit 5, and simultaneously into first and second flow cells 2,2' at a time $t_{Bb1}$, along the second conduit 15 and into the second waste reservoir 27. As it flows, the buffer fluid will also at least partially flushed out the sample buffer fluid present in the first and second flow cells 2,2', and the second conduit 15, and in the portion of the first conduit 5 between the first junction 11 and the flow cell, into the second waste reservoir 27. (Preferably, the buffer fluid flushes out all the sample buffer fluid present in the first and second flow cells 2,2', and the second conduit 15, and the portion of the first conduit between first junction 11 and the first and second flow cells 2,2', into the second waste reservoir 27).

The second buffer duration $t_{2b}$ is a measure of how long the second volume $V_2'$ of buffer fluid is injected from the first syringe pump 9 into the first and second flow cells 2,2'; the second buffer duration $t_{2b}$ in this step (b) is equal to the second buffer duration $t_{2b}$ in step (a).

The average flowrate ($V_2'/t_{2b}$) at which the second volume $V_2'$ of buffer fluid is injected in this step (b) is equal to the average flowrate $f_{2b}'$ at which the second volume $V_2'$ of buffer fluid is injected in step (a).

The duration of time interval between $t_{Bb0}$ (the time which the first volume of buffer fluid $V_1'$ begins to flow over the first and second test surfaces 3,3' in this step (c)) and $t_{Bb1}$ (the time which the second volume of buffer fluid $V_2'$ begins to flow over the first and second test surfaces 3,3' in this step (c)), is equal to the time interval between $t_{b0}$ (the time which the first volume of buffer fluid $V_1'$ begins to flow over the first and second test surfaces 3,3' in step (a)) and $t_{b1}$ (the time which the second volume of buffer fluid $V_2'$ begins to flow over the first and second test surfaces 3,3' in step (a)).

As mentioned the sensor 45 measures the binding on the first and second test surfaces 3,3' of the respective first and second flow cells 2,2' as the first and second volumes of sample buffer fluid ($V_{1B}$ $V_{2B}$) and first and second volumes of buffer fluid (V1',V2') are flowed through the first and second flow cells 2,2'. The single blank measurement binding curve is the binding curve output by the sensor 45 for the first flow cell 2, during this step (b); and the single blank reference binding curve is the binding curve output by the sensor 45 for the second flow cell 2', during this step (b).

Said sample buffer fluid provided in sample reservoir 29 does not contain any analyte which could bind to the ligands 4 on the test surface 3 of the first flow cell 2; therefore the first and second volumes $V_{1B}$ $V_{2B}$ of sample buffer fluid do not contain any analyte which could bind to the ligands 4 on the test surface 3 of the first flow cell 2. Furthermore, the buffer fluid coming from the first and/or second syringe pumps 9,19 does not contain any analyte which could bind to the ligands 4 on the test surface 3 of the first flow cell 2. Accordingly, as such, there will be no binding in either the first or second flow cells 2,2' as the first and second volumes $V_{1B}$ $V_{2B}$ of sample buffer fluid or first and second volumes of buffer fluid $V_1'$ $V_2'$ flow through the first and second flow cell 2,2'. In such a case one would expect that both the single blank measurement binding curve and single blank reference binding curve would both remain at a constant 'zero'. However in practice at least one of the single blank measurement binding curve and/or the single blank reference binding curve will comprise non-zero values; and the single blank measurement binding curve and the single blank reference binding curve will differ from one another, due to systematic errors It is understood that the single blank measurement binding curve and the single blank reference binding curve which are output by the sensor 45 in step (b) can be divided into segments for processing.

Step (c)

After, or before, the above-mentioned steps (a) and (b) have been performed, volumes of refractive index standard fluid are respectively passed through the first and second flow cells 2,2', and the sensor 45 outputs a binding curve for each respective flow cell 2,2' as these refractive index standard fluid volumes (and buffer volumes) are respectively passed through the first and second flow cells 2,2'. The refractive index standard preferably comprises a buffer fluid with an additive such as a small molecule such as DMSO or Glucose, preferably at a concentration of 0.1% v/v, or 0.5% v/v, or 1% v/v, so the refractive index of the refractive index standard fluid is different from the buffer fluid. Preferably, the diffusion properties of the additive in the refractive index standard fluid are very similar to the diffusion properties of the analytes to be tested. Preferably, the molecular weight of the additive is similar to the molecular weight of the analyte to be measured. For instance the molecular weight of the additive can be in the range of the average molecular weight of the analytes to be tested, ±20%. The volumes of refractive index standard fluid are passed through the first and second flow cells at the same rate, interval, flow rate, and duration of time, as the volumes are sample fluid (V1, V2);

for example in this example two volumes of sample fluid V1,V2 were passed through the first and second flow cells 2,2' so two volumes of refractive index standard fluid will be passed through the flow cells in this step; the interval between injecting the two volumes of refractive index standard fluid into the first and second flow cells 2,2' will be equal to the interval between the injecting the two volumes of sample fluid V1,V2 (i.e. equal to the interval between ts0 and ts1); also the flow rate and period to inject the two volumes of refractive index standard fluid will be the same as the two volumes of sample fluid V1,V2. The binding curve which the sensor 45 outputs for the first flow cell 2, as these refractive index standard fluid volumes (and buffer volumes) are respectively passed through the first flow cell 2, is referred to as the single solvent measurement binding curve; and the binding curve which the sensor 45 outputs for the second flow cell as these refractive index standard fluid volumes (and buffer volumes) are respectively passed through the second flow cell 2', is referred to as the single solvent reference binding curve. This step (c) will now, be described in more detail:

Refractive index standard fluid, is provided in the sample reservoir 29.

Most preferably all conduits, pumps, valves and the first flow cell 2 and second flow cell 2', of the microfluidic assembly 1 are rinsed, to evacuate remaining air and to clean the flow path from contaminants. To do this the third selection valve 18 is moved to its second position, and the first selection valve 8 is moved to its first position so the first selection valve 8 is open, and the second selection valve 28 is moved to its second position so the second selection valve 28 is closed. Then the plunger 19a is plunged into the receptacle 19b of the second syringe pump 19 so as to force more buffer fluid out of the second syringe pump 19. The buffer fluid which is released from the second syringe pump 19 pushes the buffer fluid into the storage conduit 30 and into the sample conduit 20, and then into the second conduit 15 and into the first flow cell 2 and second flow cell 2', and along the first conduit 5, and into the first waste reservoir 7 via the first selection valve 8. As it flows, the refractive index standard fluid also flushes out any air or contaminants present in the storage conduit 30, the sample conduit 20, the second conduit 15, the first flow cell 2, and the first conduit 5, into the first waste reservoir 7. Then, the first selection valve 8 is moved to its second position so the first selection valve 8 is closed, and the second selection valve 28 is moved to its first position so the second selection valve 28 is open. The plunger 9a is then plunged into the receptacle 9a so that buffer fluid is released from the first syringe pump 9. The buffer fluid flows out of the first syringe pump 9, through the buffer conduit 10, into the first conduit 5, and into the first flow cell 2 and second flow cell 2', and into the second conduit 15, and into the second waste reservoir 27.

At this point the sample conduit 20, the second conduit 15, the first flow cell 2 and the second flow cell 2', and the first conduit 5, and buffer conduit 10, are all filled with the buffer fluid.

The x-y table 50 is then moved so that the sample reservoir 29 is fluidly connected with the intermediate conduit 51. The third selection valve 18 is then moved to its first position so that the intermediate conduit 51 is fluidly connected with the storage conduit 30 via the third selection valve. With the third selection valve 18 in its first position, the plunger 19a of the second syringe pump 19 is moved in a direction out of receptacle 19b so as to create a negative pressure in the storage conduit 30. As a result a total pickup volume Vst of refractive index standard fluid is aspirated from the sample reservoir 29, into the intermediate conduit 51, and into the storage conduit 30 via the third selection valve 18.

Next the third selection valve 18 is moved to its second position so that the third selection valve 18 fluidly connects the storage conduit 30 and the sample conduit 20. Optionally the plunger 19a is then plunged into the receptacle 19b of the second syringe pump 19 so as to force buffer fluid out of the second syringe pump 19. The buffer fluid which is released from the second syringe pump 19 pushes some of the refractive index standard fluid out of the storage conduit 30 and into the sample conduit 20. Since the first selection pump 8 is closed, pressure provided by buffer fluid which is present in the first flow cell 2 will prevent the refractive index standard fluid from flowing along the second conduit 15 towards the first and second flow cells 2,2'; furthermore since the second selection valve 28 is in its first position so that second selection valve 28 is open, the refractive index standard fluid will flow from the sample conduit 20 and into the second conduit 15 and into the second waste reservoir 27 via the second selection valve 28.

Preferably pressure provided by the buffer fluid present in the first flow cell 2 and second flow cell 2' prevents the refractive index standard fluid from flowing along the second conduit 15 into the first and second flow cells 2,2'. In some cases a negligible amount of refractive index standard fluid may move by diffusion along a portion of the second conduit 15 in direction of the first and second flow cell 2,2'. In order to prevent or at least minimize the diffusion of refractive index standard fluid along the second conduit 15 towards the first and second flow cell 2,2', preferably a flow of buffer fluid from the first buffer reservoir 9 through the first and second flow cell 2,2' and into the second waste reservoir 27 is maintained as the refractive index standard fluid is flowing from the storage conduit 30, along the sample conduit 20 and into the second waste reservoir 27.

Preferably, the volume of refractive index standard fluid which is allowed to flow from the storage conduit 30, along the sample conduit 20 and into the second waste reservoir 27, is more than twice the volume of the sample conduit 20, but is less than the total pickup volume Vst (i.e. less than the volume of refractive index standard fluid which was aspirated from the sample reservoir 29, into the intermediate conduit 51, and into the storage conduit 30 via the third selection valve 18). Thus there is some refractive index standard fluid remaining in the storage conduit 30.

Thus at this stage preferably the sample conduit 20 has been rinsed with the refractive index standard fluid; and is filled with refractive index standard fluid. At this stage preferably the buffer conduit 10, the first and second flow cell 2,2' all contain buffer fluid only; while preferably the sample conduit 20 contains refractive index standard fluid only.

Before the following steps are carried out and also during carrying of the following steps, the sensor 45 attached to the first and second flow cells 2, 2' is configured to output a binding curve for each of the first and second flow cells 2,2'. The binding curve output by the sensor 45 for the first flow cell 2, during this step (c), will be referred to hereafter as the single solvent measurement binding curve. The binding curve output by the sensor 45 for the second flow cell 2', during this step (c), will be referred to hereafter as the single solvent reference binding curve. There will be a difference between the single solvent measurement binding curve and the single solvent reference binding curve due to the fact that the volume within the first flow cell 2' will be different to the volume within the second flow cell 2' (since there are ligands 4 present in the first flow cell 2 which occupy part of the volume within the first flow cell; whereas there are no ligands in the second flow cell 2' (or if there are ligands on the second test surface 3' of the second flow cell 2' then there will be of a different type to the ligands on the first test surface 3 and may also be a different amount of ligands on the second test surface 3'); these differences in volumes within the first and second flow cells 2,2', lead to different sensor binding curve outputs.

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a first volume $V_{1s}$ of buffer fluid out of the second syringe pump 19, wherein the first volume $V_{1s}$ is smaller than the total pickup volume Vst. The buffer fluid which is released from the second syringe pump 19 pushes a corresponding first volume $V_{1s}$ of the refractive index standard fluid out of the storage conduit 30 and into the sample conduit 20.

The refractive index standard fluid which is now passing into the sample conduit 20 flows into the second conduit 15, flows simultaneously into the first and second flow cells 2,2' at a time $t_{r0}$, and along the first conduit 5, and into the first waste reservoir 7 via the first selection valve 8. As it flows, the refractive index standard fluid also at least partially flushes out buffer fluid present in the first and second flow cells 2,2', and the first conduit 5, into the first waste reservoir 7 (preferably the refractive index standard fluid flushes out all the buffer fluid present in the first and second flow cells 2,2', and the first conduit, and in the portion of the second conduit 15 between the second junction 21 and the first flow cell 3, into the first waste reservoir 7).

Thus, at this stage the sample conduit 20, the portion of the second conduit 15 between the second junction 21 and the first and second flow cells 2,2', and the first conduit 5 all contain refractive index standard fluid only.

The first volume $V_{1s}$ of refractive index standard fluid is equal to the first volume V1 of sample fluid in step (a).

The duration of time ($t_{1s}$) the first volume $V_{1s}$ of refractive index standard fluid flows over the first and second test surfaces 3,3' of the first and second flow cells 2,2' is equal to the first analyte duration $t_{1a}$ in step (a).

The average flowrate ($V_{1s}/t_{1a}$) at which the first volume $V_{1s}$ of refractive index standard fluid is injected is equal to the to the average flowrate of the first sample volume $f_{1a}$ in step (a).

Next the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19a is fixed so as to prevent the flow of fluid into or out of the receptacle 19b of the second syringe pump 19. The plunger 9a of the first syringe pump 9 is then plunged into the receptacle 9b so that a first volume $V_1'$ of buffer fluid (which is free from analyte) is released from the first syringe pump 9. The first volume $V_1'$ of buffer fluid is equal to the first volume $V_1'$ of buffer fluid in step (a). The buffer fluid released from the first syringe pump 9 will flow through the first conduit 5, simultaneously into first and second flow cells 2,2' at a time $t_{rb0}$, and into the second conduit 15 and into the second waste reservoir 27. As it flows, the buffer fluid also at least partially flushes out refractive index standard fluid present in the first and second flow cells 2,2', and the second conduit 15, and the portion of the first conduit between first junction 11 and the flow cell 2, into the second waste reservoir 27 (preferably the buffer fluid flushes out all the refractive index standard fluid present in the first and second flow cells 2,2', and the second conduit 15, and the portion of the first conduit between first junction 11 and the first and second flow cells 2,2', into the second waste reservoir 27).

The first buffer duration $t_{1b}$ is a measure of how long the first volume $V_1'$ of buffer fluid is injected from the first syringe pump 9 into the first and second flow cells 2,2'; the first buffer duration $t_{1b}$ in the above step is equal to the first buffer duration $t_{1b}$ in step (a).

The average flowrate ($V_1'/t_{1b}$) at which the first volume $V_1'$ of buffer fluid is injected in this step is equal to the average flowrate $f_{1b}'$ at which the first volume $V_1'$ of buffer fluid is injected in step (a).

Next the first selection valve 8 is moved to its first position (i.e. the first selection valve 8 is opened) so that fluid can pass from first conduit 5 into the first waste reservoir 7 and preferably the second selection valve 28 is moved to its second position so that it is closed. With the third selection valve 18 still in its second position, the plunger 19a is plunged into the receptacle 19b of the second syringe pump 19 so as to force a second volume $V_{2s}$ of buffer fluid out of the second syringe pump 19, wherein the second volume $V_{2s}$ is smaller than the total pickup volume Vst. The second volume $V_{2s}$ of buffer fluid which is released from the second syringe pump 19 pushes a corresponding second volume $V_{2s}$ of the refractive index standard fluid remaining in the storage conduit 30, out of the storage conduit 30 and into the sample conduit 20.

Since the first selection valve 8 is in its second position (i.e. the first selection valve 8 is open) the buffer fluid present in the first flow cell 2 no longer provides a pressure which prevents the refractive index standard fluid from flowing along the second conduit 15 into the first and second flow cells 2,2'. Accordingly the second volume $V_{2s}$ of refractive index standard fluid which is now passing into the sample conduit 20 flows into the second conduit 15, and flows simultaneously into the first and second flow cells 2,2' at a time $t_{r1}$, and along the first conduit 5, and into the first waste reservoir 7 via the first selection valve 8. As it flows, the second volume $V_{2s}$ of refractive index standard fluid also at least partially flushes out buffer fluid present in the first and second flow cells 2,2', and the first conduit 5, into the first waste reservoir 7.

The duration of time interval between to (the time which the first volume $V_{1s}$ of the refractive index standard fluid begins to flow over the first and second test surfaces 3,3') and $t_{r1}$ (the time which the second volume $V_{2s}$ of the refractive index standard fluid begins to flow over the first and second test surfaces 3,3') is equal to the time interval between $t_{s0}$ (the time which the first volume V1 of the sample fluid begins to flow over the first and second test surfaces 3,3') and $t_{s1}$ (the time which the second volume V2 of the sample fluid begins to flow over the first and second test surfaces 3,3') in step (a).

The second volume $V_{2s}$ of the refractive index standard fluid is equal to the second volume V2 of sample fluid in step (a).

The duration of time ($t_{2s}$) the second volume $V_{2s}$ of refractive index standard fluid flows over the first and second test surfaces 3,3' of the first and second flow cells 2,2' is equal to the second analyte duration $t_{2a}$ in step (a).

The average flowrate ($V_{2s}/t_{2a}$) at which the second volume $V_{2s}$ of first refractive index standard fluid volume is injected is equal to the to the average flowrate of the first sample volume $f_{2a}$ in step (a).

Next, preferably, the first selection valve 8 is moved to its second position so that first selection valve 8 is closed and the second selection valve 28 is moved to its first position so that the second selection valve can allow fluid to flow from the second conduit 15 into the second waste reservoir 27. Preferably the third selection valve 18 is still in its second position and the position of the plunger 19*a* is fixed so as to prevent the flow of fluid into or out of the receptacle 19*b* of the second syringe pump 19. The plunger 9*a* of the first syringe pump 9 is then plunged into the receptacle 9*b* so that a second volume of buffer fluid $V_2'$ is ejected from the first syringe pump 9. The second volume of buffer fluid $V_2'$ released from the first syringe pump 9 will flow through the first conduit 5, and simultaneously into first and second flow cells 2,2' at a time $t_{rb1}$, along the second conduit 15 and into the second waste reservoir 27. As it flows, the buffer fluid will also at least partially flushed out refractive index standard fluid present in the first and second flow cells 2,2', and the second conduit 15, and in the portion of the first conduit 5 between the first junction 11 and the flow cell, into the second waste reservoir 27 (preferably the buffer fluid flushes out all the refractive index standard fluid present in the first and second flow cells 2,2', and the second conduit 15, and the portion of the first conduit between first junction 11 and the first and second flow cells 2,2', into the second waste reservoir 27).

The second buffer duration $t_{2b}$ is a measure of how long the second volume $V_2'$ of buffer fluid is injected from the first syringe pump 9 into the first and second flow cells 2,2'; the second buffer duration $t_{2b}$ in the above step is equal to the second buffer duration $t_{2b}$ in step (a).

The average flowrate ($V_2'/t_{2b}$) at which the second volume $V_2'$ of buffer fluid is injected in this step is equal to the average flowrate $f_{2b}'$ at which the second volume $V_2'$ of buffer fluid is injected in step (a).

The duration of time interval between $t_{rb0}$ (the time which the first volume of buffer fluid $V_1'$ begins to flow over the first and second test surfaces 3,3' in this step (c)) and $t_{rb1}$ (the time which the second volume of buffer fluid $V_2'$ begins to flow over the first and second test surfaces 3,3' in this step (c)), is equal to the time interval between interval between $t_{b0}$ (the time which the first volume of buffer fluid $V_1'$ begins to flow over the first and second test surfaces 3,3' in step (a)) and $t_{b1}$ (the time which the second volume of buffer fluid $V_2'$ begins to flow over the first and second test surfaces 3,3' in step (a)).

As mentioned the sensor measures the binding on the first and second test surfaces 3,3' of the respective first and second flow cells 2,2' as the first and second volumes of refractive index standard fluid ($V_{1s}, V_{2s}$) and first and second volumes of buffer fluid (V1',V2') are flowed through the first and second flow cells 2,2'. The single solvent measurement binding curve is the binding curve output by the sensor 45 for the first flow cell 2, during this step (c); and the single solvent reference binding curve is the binding curve output by the sensor 45 for the second flow cell 2', during this step (c). Said refractive index standard fluid does not contain any analyte which could bind to the ligands 4 on the test surface 3 of the first flow cell 2; therefore the first and second volumes $V_{1s}, V_{2s}$ of refractive index standard fluid do not contain any analyte which could bind to the ligands 4 on the test surface 3 of the first flow cell 2. Furthermore, the buffer fluid does not contain any analyte which could bind to the ligands 4 on the test surface 3 of the first flow cell 2.

Accordingly, as such, there will be no binding in either the first or second flow cells 2,2' as the first and second volumes $V_{1s}, V_{2s}$ or first and second volumes of buffer fluid $V_1' V_2'$ flow through the first and second flow cell 2,2'. In such a case one would expect that both the single solvent measurement binding curve and solvent reference binding curve would both remain at a constant 'zero'; however in practice this is not the case. Both the single solvent measurement binding curve and the single solvent reference binding curve will comprise non-zero values because the sensor 45 is sensitive to refractive index changes, and the refractive index standard fluid has a different refractive index than the buffer fluid. Importantly, both the single solvent measurement binding curve and the single solvent reference binding curve will differ from one another due to the fact that the free volume within the first flow cell 2' will be different from the free volume within the second flow cell 2' (since there are ligands 4 present in the first flow cell 2 which occupy part of the volume within the first flow cell; whereas there are no ligands in the second flow cell 2' (or if there are ligands on the second test surface 3' of the second flow cell 2' then there will be of a different type to the ligands on the first test surface 3 and may also be a different amount of ligands on the second test surface 3'), therefore the refractive index difference between the refractive index standard fluid and the buffer fluid will have a different impact on the single solvent measurement binding curve than on the single solvent reference binding curve.

It is understood that the single solvent measurement binding curve and the single solvent reference binding curve which are output by the sensor 45 in step (c) can be divided into segments for processing.

Importantly, it should be understood that steps (a)-(c) described above may be carried out in any order. The invention is not limited to carrying out steps (a)-(c) in the order in which they are recited in the above paragraphs. For example, in another embodiment step (c) may be carried out first, followed by carrying out step (b) followed by carrying out step (a); in another embodiment step (b) may be carried out first, followed by carrying out step (c) followed by carrying out step (a); in another embodiment step (a) may be carried out first, followed by carrying out step (b) followed by carrying out step (c).

Step (d)

The single reference binding curve and the single measurement binding curve obtained from step (a); and the single blank reference binding curve and single blank measurement binding curve obtained from step (b); and the single solvent reference binding curve and the single solvent measurement binding curve obtained from step (c), are then processed in order to determine an adjusted binding curve as follows:

Step 1: The single reference binding curve is subtracted from the single measurement binding curve, to provide a difference curve.

Step 2: The single blank reference binding curve is subtracted from the single blank measurement binding curve to provide a blank difference signal.

Step 3: The single solvent reference binding curve is subtracted from the single solvent measurement binding curve to provide a solvent difference signal.

Step 4: The difference curve is zeroed with respect to the y-axis by subtracting the average y-value of the difference curve at a zeroing time ty from the difference curve, resulting in a zeroed single binding curve (zsbc). Preferably, the zeroing time ty is prior to the passing the first volume of the sample fluid V1 into the first and second flow cells 2,2'.

Step 5: The blank difference signal is zeroed with respect to the y-axis by subtracting the average y-value of the blank difference signal at the zeroing time ty from the blank difference signal, resulting in a zeroed single blank binding curve (zsbbc).

Step 6: The solvent difference signal is zeroed with respect to the y-axis by subtracting the average y-value of the solvent difference signal at a zeroing time ty from the solvent difference signal, resulting in a zeroed single solvent binding curve (zssbc)

Step 7 (optional): Next, optionally, solvent correction is carried out, which involves:

(i) Determining the average solvent difference ('sdiff').

In one embodiment the average solvent difference ('sdiff') is determined by: determining the average value of the solvent difference signal at a solvent time ts, wherein the average value of solvent difference signal at a solvent time ts is the average solvent difference ('sdiff'). Most preferably the time ts is a time instant which lies mid-way in the second analyte duration t2a (i.e. in the middle of the time the second volume of sample fluid V2 is flowing simultaneously through the first and second flow cells 2,2'). Furthermore, the average value of the single solvent reference binding curve at the solvent time ts is determined (the average value of the single solvent reference binding curve d at the solvent time ts is denoted as 'srbc' hereafter).

In another embodiment the average solvent difference ('sdiff') is determined by: first determining the average value of the single solvent measurement binding curve at the solvent time ts (the average value of the single solvent measurement binding curve at the solvent time ts is denoted as 'smbc' hereafter). Then, determining the average value of the single solvent reference binding curve at the solvent time ts (the average value of the single solvent reference binding curve d at the solvent time ts is denoted as 'srbc' hereafter). Then, the average solvent difference (denoted as 'sdiff') is determined as follows:

$$sdiff=smbc-srbc$$

(ii) The above-mentioned step (c) is repeated to plurality of times to provide a plurality of different single solvent reference binding curves and the single solvent measurement binding curves; and repeating the above-mentioned step (i) for each of the plurality of different single solvent reference binding curves and the single solvent measurement binding curves, to yield a set of $srbc_i$, $sdiff_i$ relating the average solvent difference sdiff to the average value srbc of the single solvent reference binding curve for all measured solvent measurements.

(iii) A solvent correction function fs is then established by fitting a polynomial function through the set of $srbc_i$, $sdiff_i$ to approximate sdiff=fs (srbc). For example, if in step (v) is repeated for three different volumes of refractive index standard fluid volumes, then there will be three different sets of srbc, sdiff values; the solvent correction function fs is an approximation, fitted to those three different sets of srbc, sdiff values, establishing the described analytical relation.

(iv) A solvent corrected single binding curve (denoted as 'scsbc') is obtained by applying the solvent correction function (fs) to the single reference binding curve (denoted as 'srbc') and subtracting it from the zeroed single binding curve (zsbc) as follows:

$$scsbc=zsbc-fs(srbc),$$

(v) A solvent corrected single blank binding curve (denoted as 'scsbbc') is obtained by applying the solvent correction function (fs) to the single blank reference binding curve (denoted as 'sbrbc') and subtracting the result from the zeroed single blank binding curve (zsbbc) as follows:

$$scsbbc=zsbbc-fs(sbrbc),$$

It should be understood that the above-mentioned solvent correction steps (i)-(vi) are optional.

Step 8: Finally, the curves are preferably blank referenced so as to obtain the adjusted binding curve (denoted as 'abc'):

In one embodiment the adjusted binding curve ('abc') is obtained by subtracting the zeroed single blank binding curve (zsbbc) from zeroed single binding curve (zsbc) as follows:

$$abc=zsbc-zsbbc$$

In another embodiment, in which the above-mentioned solvent correction steps (i)-(vi) are carried out, the adjusted binding curve is obtained by subtracting the solvent corrected single blank binding curve (denoted as 'scsbbc') from the solvent corrected single binding curve (denoted as 'scsbc') follows:

$$abc=scsbc-scsbbc$$

Figure 3:
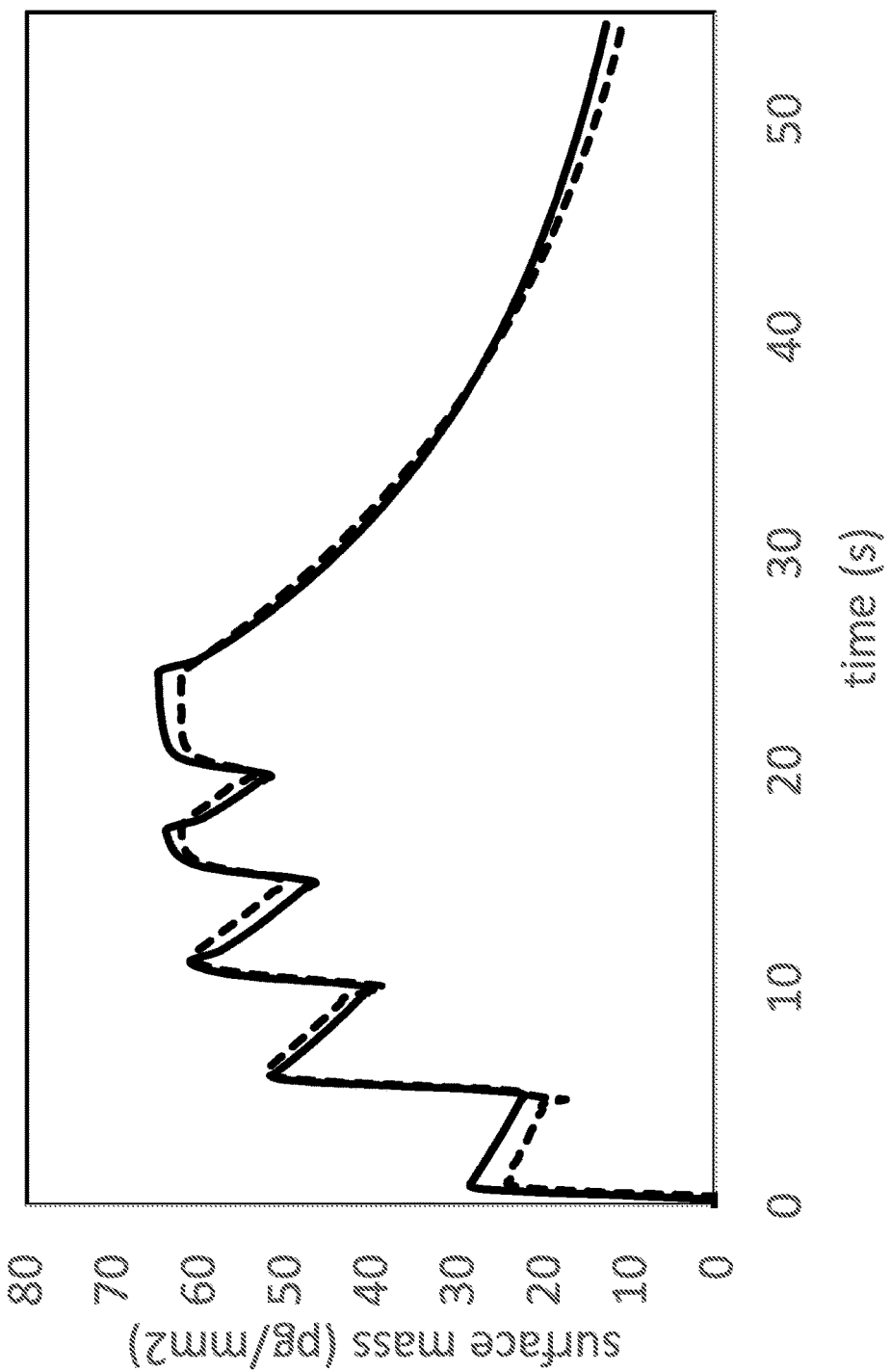
FIG. 3 shows the simulated binding curve (dashed line) for kinetic parameters Rmax, ka, kd which best approximate an adjusted binding curve (solid line) which was obtained using the a method according to the present invention.

FIG. 3 shows the adjusted binding curve (solid line) obtained after the above mentioned steps (a)-(d) have been carried out (including carrying out solvent correction).

Step (e)

The adjusted biding curve is then used to determine the kinetic parameters, such as the association rate constant ka, and the dissociation rate constant kd, and to characterize the interaction between the analyte in the volumes of sample fluid which were flowed through the first flow cell 2 (and second flow cell 2') (specifically which was in the first and second volumes of sample fluid V1, V2) and the ligands 4 on the first test surface 3 of the flow cell 2.

In one embodiment the adjusted binding curve may be processed using any suitable, known means in the art for processing reaction curves to determine kinetic parameters.

In a preferred embodiment in order to determine the kinetic parameters ka and kd, a model describing the binding is fitted to the adjusted binding curve.

In one embodiment fitting a model to the adjusted binding curve preferably includes the steps of determining an adjusted solvent curve (denoted as 'asc') by subtracting the single blank reference binding curve (sbrbc) from the single solvent reference binding curve (ssrbc) as follows:

$$asc=ssrbc-sbrbc$$

Then, the adjusted solvent curve is zeroed with respect to the y-axis by subtracting the average y-value of the adjusted solvent curve at a zeroing time ty from adjusted solvent curve, resulting in a zeroed adjusted solvent curve (zasc). Preferably, the zeroing time ty is prior to the passing the first volume of the sample fluid V1 into the first and second flow cells 2,2'

In a preferred embodiment, a single concentration curve is then established by dividing the zeroed adjusted solvent curve by the average maximum value of the adjusted solvent curve to obtain a normalized solvent curve, and then multiplying the normalized solvent curve by the predetermined concentration $c_0$ of the analyte which was in the first and second volumes of sample fluid V1,V2 (recall that each volume of sample fluid has the same predetermined concentration $c_0$ of the analyte). Preferably, the average maximum value of the adjusted solvent curve is obtained by determining the average value of the adjusted solvent curve at the solvent time ts, wherein the average value of the adjusted solvent curve at a solvent time ts is the average maximum value of the adjusted solvent curve.

Assuming a 1:1 binding model, the binding of analyte which was in the volumes of sample fluid which were flowed through the first and second flow cells 2,2' in step (a) (specifically, in this example, analyte in the first and second volumes of sample fluid (V1,V2)), to the ligands 4 on the first test surface 3 of the first flow cell 2, can be described by the following differential equation:

$$\frac{dR}{dt} = k_a c(R_{max} - R) - k_d R$$

The above differential equation is numerically integrated using the value of the single concentration curve at each time step as the variable 'c', and assuming initial guesses for the variables Rmax and the parameters ka and kd, to yield a simulated binding curve (denoted as 'sbc').

Then the chi square ($\chi^2$) of the simulated binding curve ('sbc') is determined by:

$$\chi^2 = \sum \frac{(sbc_i - abc_i)^2}{n}$$

The chi square ($\chi^2$) of the simulated binding curve ('sbc') is a measure of how well the simulated binding curve ('sbc') approximates the adjusted binding curve (abc). By using estimators or optimization schemes, such as the well known Levenberg-Marquardt algorithm, which minimize the chi square, the parameters Rmax, ka, kd which best approximate the adjusted binding curve (abc) are found. Said parameters Rmax, ka, kd which best approximate the adjusted binding curve (abc) define the parameters Rmax, ka, kd which characterize the interaction between the analyte in the volumes of sample fluid which were flowed through the first flow cell 2 (specifically, in this example, analyte in the first and second volumes of sample fluid V1, V2) and the ligands 4 on the first test surface 3 of the flow cell 2.

FIG. 3 shows the simulation (dashed line) for the parameters Rmax, ka, kd=$5.89 \times 10^{-2}$ $s^{-1}$ which best approximate the adjusted binding curve (solid line), in this example the parameters which best approximate the adjusted binding curve (solid line) are Rmax=63.3 pg/mm2, ka=$2.66 \times 10^4$ $M^{-1}s^{-1}$, kd=$5.89 \times 10^{-2}$ $s^{-1}$.

Preferably, the above-mentioned steps (a)-(e) are repeated for multiple different types of sample fluids for determining binding and measuring kinetics for different types of analytes.

Advantageously, the total measurement time using the method of the present invention is short with respect to the prior art; a new sample can start to be tested a short time after a previous sample has started to be tested; in other words a second volume of sample fluid can be passed over the first testing surface 3 of the first flow cell 2 soon after a first volume of sample fluid has been passed over the first testing surface 3. Further a different type of sample fluid containing a different type of analyte can tested soon (about 5 seconds) after testing a previous sample fluid. In other words very soon (about 5 seconds) after carrying out the above-mentioned steps (a)-(e) for one type of sample fluid containing one type of analytes, to determine binding and measuring kinetics for that type of analytes, the above-mentioned steps (a)-(e) for another type of sample fluid containing another type of analytes, to determine binding and measuring kinetics for that other type of analytes can be carried out.

It should be understood that the method of the present invention may be carried out using an assembly that may comprise only one single flow cell; in this case steps (a)-(c) are performed before providing ligands on the test surface of the one single flow cell so as to obtain the single reference binding curve from step (a), the single blank reference binding curve from step (b), and the single solvent reference binding curve from step (c). Thereafter ligands are provided on the test surface of the one single flow cell, and steps (a)-(c) are repeated so as to obtain the single measurement binding curve from step (a), the single blank measurement binding curve obtained from step (b); and the single solvent measurement binding curve from step (c). It follows that in a variation of the assembly 1 embodiment show in FIG. 1, the assembly may alternatively comprise a single flow cell, instead of having a first and second flow cell 2,2'.

It should be understood that the method of the present invention may be carried out using any of the assemblies described in WO2017187325A1.

It should be understood that the method of the present invention may be carried out using various embodiments of microfluidic assemblies commonly used in the biosensings field, such as, for example any of the assemblies described in WO2014009286A1 or WO2013055281, provided that the assembly in question allows consecutively injecting volumes of sample fluid containing the analyte and volumes of buffer fluid (free from analyte) into the flow cells.

Preferably, in the method of the present invention each of the sample fluid volumes which as passed through the first and second flow cells come from the same single sample reservoir 29. The single sample reservoir 29 may be a well of a microtiter plate. In the most preferred embodiment all of said respective volumes of sample fluid which are flowed over the test surface of the flow cell, are aspirated from the same single receptacle before any volume of sample fluid is flowed over the test surface of the flow cell; in other words there is a single aspiration step, which is carried out before any volume of sample fluid is flowed over the test surface of the flow cell, in which a single volume of sample fluid is aspirated from the single receptacle, and all of the sample fluids which are subsequently flowed over the test surface of the flow cell come from that single volume of sample fluid which was aspirated. In other words each volume of sample fluid which is flowed over the test surface of the flow cell is a portion of the single volume of sample fluid which was aspirated from the single receptacle.

In a preferred embodiment of the method of the present invention, the sum of the volumes of sample fluid (containing the analyte) $\Sigma V_i$ which are flowed through the first and second flow cells 2,2', is smaller than the total pickup volume $V_t$.

Surprisingly, in the present invention, even though the ligands 4 on the first testing surface 2 are only contacted with one common analyte concentration (since each of the volumes of sample fluid flowed into the first and second flow cells 2,2' all have the same predetermined concentration $c_o$ of analyte), information about kinetic parameters such as association rate constant ka and dissociation rate constant kd can be obtained from a measurement according to the method of the present invention.

In a preferred embodiment, the first analyte duration $t_{1a}$ is the shortest of all analyte durations $t_{ia}$, and the last analyte duration $t_{Na}$ is the longest of all analyte durations $t_{ia}$, for allowing a measurement of the broadest kinetic space possible in the shortest amount of time. In a further preferred embodiment, the analyte durations increase in an exponential manner from first analyte duration $t_{1a}$ to the last analyte duration $t_{Na}$. For instance, in an embodiment wherein five volumes of sample fluid are flowed into the first and second flow cells 2,2', the second analyte duration $t_{2a}$ is three times as long as the first analyte duration $t_{1a}$, a third analyte duration $t_{3a}$ is three times as long as the second analyte duration $t_{2a}$, a fourth analyte duration $t_{4a}$ is three times as long as the third analyte duration $t_{3a}$, and a fifth analyte duration $t_{5a}$ is three times as long as the fourth analyte duration $t_{4a}$. As already described in detail above in step (a) the analyte duration is the duration of time the volume of sample fluid flows over the first and second test surfaces 3,3' of the first and second flow cells 2,2'; so for example the third analyte duration $t_{3a}$ is the duration of time the third volume of sample fluid flows over the first and second test surfaces 3,3' of the first and second flow cells 2,2'.

In a further preferred embodiment, the last buffer duration $t_{bN}$ is the longest of all buffer durations $t_{bi}$ in order to allow dissociation of the analyte from ligands 4 in the first flow cell 2, before injecting a next volume of sample fluid. As already described above in detail in step (a) the buffer duration is how long the buffer fluid is injected from the first syringe pump 9 into the first and second flow cells 2,2'; it follows that the last buffer duration is how long the last volume of buffer fluid which is to be flowed through the first and second flow cells 2,2' is injected into the first and second flow cells 2,2' from the first syringe pump 9.

In a preferred embodiment, the last buffer duration $t_{bN}$ corresponds to approximately $1/k_{d,\ min}$ or $2/k_{d,\ min}$ or $3/k_{d,\ min}$, where $k_{d,\ min}$ is the smallest dissociation rate constant within the kinetic region of interest for a particular measurement. As an example, when characterizing binders in the affinity range from 10 nM to 10 µM, the smallest dissociation constant within the region of interest for binders in this affinity range can be chosen to be $k_{d,\ min}=1e-2\ s^{-1}$, and the last buffer duration can be chosen to be $3/k_{d,\ min}=300\ s$.

In a further preferred embodiment especially suited for tight binders such as in the affinity range of 1 pM to 1 nM ("picomolar binders"), the test surface 2,2' of the flow cells 3,3' are regenerated either by using regeneration reagents promoting dissociation or by removing and re-capturing ligands, and the last buffer duration $t_{bN}'$ corresponds to approximately $1/(10\ k_{d,\ min})$ or $1/(20\ k_{d,\ min})$ or $1/(50\ k_{d,\ min})$. As an example, the smallest dissociation constant within the region of interest for picomolar binders can be chosen to be $k_{d,\ min}=1e-5\ s^{-1}$, and the last buffer duration can be chosen to be $1/(50\ k_{d,\ min})=2,000\ s$.

In a further preferred embodiment, the binding curve output from the sensor 45 in step (a), and/or step (b), and/or step (c) are evaluated and corrected for systematic errors in real time. In one embodiment last buffer duration $t_{bN}$ in step (a) is increased in case single measurement binding curve has not yet returned to a predefined baseline. Preferably the last buffer duration $t_{bN}$ in step (a) is until the single measurement binding curve has returned to a predefined baseline.

In a further preferred embodiment, the last buffer duration $t_{bN}$ is the longest of all buffer durations $t_{bi}$, and the first buffer duration $t_{b1}$ is the second longest of all buffer durations $t_{bi}$. In a further preferred embodiment, the buffer durations decrease in an exponential manner from first buffer duration $t_{b1}$ to the second last buffer duration $t_{bN-1}$. For instance, in an embodiment wherein '6' volumes of buffer fluid are to be passed into the first and second flow cells 2,2', then the second buffer duration $t_{b2}$ is three times shorter than the first buffer duration $t_{b1}$, a third buffer duration $t_{b3}$ is three times shorter than the second buffer duration $t_{b2}$, a fourth buffer duration $t_{b4}$ is three times shorter than the third buffer duration $t_{b3}$, and a fifth buffer duration $t_{b5}$ is three times as long as the fourth analyte duration $t_{b4}$.

In a further preferred embodiment, the shortest buffer duration $tb_{min}$ corresponds to approximately $1/k_{d,\ max}$ or $2/k_{d,\ max}$ or $3/k_{d,\ max}$, where $k_{d,\ max}$ is the greatest dissociation rate constant, corresponding to the fastest dissociation to be measured, such as the binding curve returns almost to baseline for the fastest off-rates to be measured.

In a further preferred embodiment, the shortest buffer duration $t_{min}$ corresponds to approximately the fall time of the analyte $\tau_a'$, where the fall time of the analyte $\tau_a'$ is the time from start of injection of the buffer fluid to the time the concentration of the analyte on the first test surface 3 of the first flow cell 2, has been reduced to an average of 5% of the predetermined concentration $c_0$. In the most preferred embodiment the refractive index fluid comprises an additive which has similar diffusion properties as the analyte, this enables the fall time of the analyte $\tau_a'$ to be measured using solvent binding curves as the fall time of the refractive index fluid is at least close to the fall time of the analyte $\tau_a'$. Preferably, the fall time of the analyte $\tau_a'$ is measured on the zeroed adjusted solvent curve (zasc) around time $t_{rbN}$ (the time which the last volume of buffer fluid $V_2'$ begins to flow over the first and second test surfaces 3,3' in above step (c)). Preferred values for the shortest buffer duration $t_{min}$ are for instance $t_{min}'=1\times\tau_a'$, or $t_{min}'=0.75\times\tau_a'$, or $t_{min}'=1.25\times\tau_a'$ or $t_{min}'<2\times\tau_a'$ or $t_{min}'<3\times\tau_a'$. Thereby, the fastest possible off-rates can be determined.

In a further preferred embodiment, the first analyte duration $t_{a1}$ is shorter than the rise time of the analyte $\tau_a$, wherein the rise time of the analyte $\tau_a$ is the time from start of injection of a volume of sample fluid to the time the concentration of the analyte at the first test surface 2 of the first flow cell has reached an average 95% of the predetermined concentration $c_0$. In the most preferred embodiment the refractive index fluid comprises an additive which has similar diffusion properties as the analyte, this enables the rise time of the analyte $\tau_a$ can be measured using solvent binding curves as the rise time of the refractive index fluid is at least close to the rise time of the analyte $\tau_a$. Preferably, the rise time of the analyte $\tau_a$ is measured on the zeroed adjusted solvent curve (zasc) around time $t_{rN}$ (the time which the last volume $V_{Ns}$ of the refractive index standard fluid begins to flow over the first and second test surfaces 3,3'). Preferred values for the shortest buffer duration $t_{min}$ are for instance $t_{a1}=\tau_a/2$, or $t_{a1}=\tau_a/5$, or $t_{a1}=\tau_a/10$. Thereby, the effective concentration at the sensor surface is reduced, allowing the measurement of faster on-rates.

In a further preferred embodiment, the parameters of the injection sequence are optimized using computer simulations, such as Monte-Carlo simulations, for maximizing difference in shape of the binding curves, for interactions within a region of interest of the kinetic space.

Figure 4:
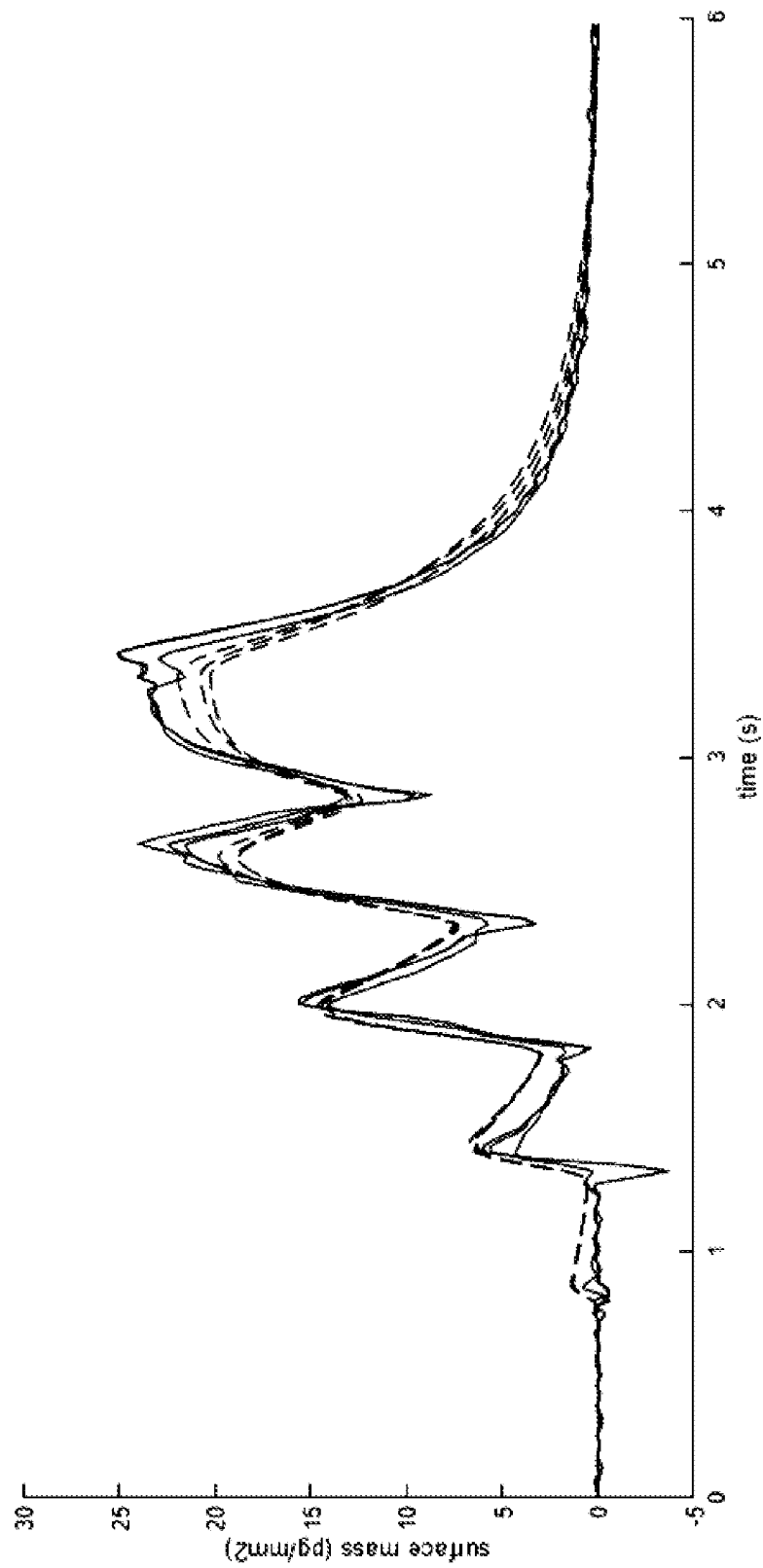
FIG. 4 shows an example of an adjusted binding curve (solid line) and corresponding best approximate simulated binding curve (dashed line) which was obtained using a method according to the present invention.

FIG. 4 provides the result of an example measurement according to the present invention, highlighting the suitability of the invention for high throughput screening of weak binders, which typically lie in the affinity range of 1 µM to 1 mM. In this example, the afore-mentioned steps of injecting a sample fluid volume (containing the analyte) and injecting buffer fluid volume (which is free from analyte) have been carried out '5' times (i.e. '5' sample fluid volumes and '5' buffer fluid volumes have been flowed through the first and second flow cells 2,2'). The x-axis of the graph denotes time in seconds, and the y-axis denotes surface mass in pg/mm2.

FIG. 4 depicts three adjusted binding curves (solid lines) corresponding to a triplicate measurement of the interaction of a a 6-mer oligonucleotide (5'-CAGTGC-3'; 1792 Da) with a biotinylated 34-mer (bio-34; 5'-[Btn]TTTTTG-GAAACTGTATTGGCACTGAGTAGACTCC-3'; 11 kDa), and corresponding simulated binding curves (dashed lines) which best fits the kinetic parameters to the adjusted binding curves. The measurement has been obtained using a Creoptix WAVEdelta system at an acquisition frequency of 40 Hz and 15° C. flow cell temperature. A PCP-S WAVEchip was used comprising four parallel flow cells. The device was modified in its measurement processes to allow multiple injections from a single sample reservoir. Prior to the depicted measurement, a biotinylated 34-mer (bio-34; 5'-[Btn]TTTTTGGAAACTGTATTGGCACTGAGTA-GACTCC-3'; 11 kDa, "target") was captured (at a density of ~300 pg/mm2) as ligands on Streptavidin onto a PCP-S WAVEchip on the sensor surfaces of flow cells 2 and 3. Flow cell 1 and flow cell 4 were left empty and used as reference. PBS buffer pH 7.4 containing 0.05% Tween-20 was used as buffer. The first volume of the sample fluid V1 was injected with a first analyte duration $t_{1a}$ of 31.25 ms, followed by a first volume of buffer fluid V1' with a first buffer duration $t_{1b}$ of 0.46875 s, followed by the second volume of the sample fluid V2 with a second analyte duration $t_{2a}$ of 0.625 ms, followed by a second volume of buffer fluid V2' with a second buffer duration $t_{2b}$ of 0.4375 s, followed by a third volume of the sample fluid V3 with a third analyte duration $t_{3a}$ of 0.125 s, followed by a third volume of buffer fluid V3' with a third buffer duration tab of 0.375 s, followed by a fourth volume of the sample fluid V4 with a fourth analyte duration $t_{4a}$ of 0.25 s, followed by a fourth volume of buffer fluid V4' with a fourth buffer duration $t_{4b}$ of 0.25 s, followed by a fifth volume of the sample fluid V5 with a fifth analyte duration $t_{5a}$ of 0.5 s, followed by a fifth volume of buffer fluid V5' with a fifth buffer duration $t_5$b of 2.5 s.

In this example, the first analyte duration $t_{a1}$ of 31.25 ms is shorter than the rise time of the analyte $\tau_a$ (measured to be 125 ms around the time), in particular $t_{a1}=\tau_a/4$, and the fourth buffer duration $t_{4b}$ is the shortest buffer duration $t_{min}$ at 250 ms, and corresponds to approximately the fall time of the analyte $\tau_a'$ (measured to be 150 ms).

First, for referencing purposes, buffer blanks were injected from a single vial as analyte into all four flow cells in parallel at a flow rate of 100 μl/min per flow cell in alternation with buffer and the corresponding single blank measurement binding curve and the single blank reference binding curve were recorded by the sensor (not shown). Then, a 6-mer oligonucleotide (5'-CAGTGC-3'; 1792 Da) was then injected at 100 μM concentration from a single vial as analyte into all four flow cells in parallel at a flow rate of 100 μl/min per flow cell in alternation with buffer fluid in triplicate (i.e. the same measurement was repeated three times) and the corresponding single measurement binding curves as well as the single reference binding curves were recorded by the sensor. Then DMSO diluted to 1% concentration in buffer was injected as analyte from a single vial into all four flow cells in parallel at a flow rate of 100 ul/min per flow cell in alternation with buffer and the corresponding single solvent measurement binding curve and single solvent reference binding curve were recorded by the sensor (not shown). Then, the adjusted binding curves (solid lines) were obtained using step (d) steps 1-8 above for each set of single measurement binding curves and single reference binding curves. Then, the adjusted biding curves were then used to determine the kinetic parameters association rate constant ka, and the dissociation rate constant kd, for each of the three adjusted binding curves, using step (e) above. The average and standard deviation of the kinetic parameters determined from the fits of the three binding curves to the interaction model were $k_a$, =5.95±0.53×10$^4$ M−1s−1, $k_d$=2.32±0.09 s−1, and a $R_{max}$ of 29.7±1.8 pg/mm$^2$.

Advantageously, in above example the kinetic parameters of the interaction have been determined with a total measurement time of 5 seconds only, allowing for a high throughput in determining kinetic rates in a screen.

In a further preferred embodiment, a neural network is trained using simulation data covering a given range of kinetic parameters for a given set of injection sequence parameters and a given set of timing parameters $t_1, t_2 \ldots t_N$ and $t_1', t_2' \ldots t_N'$ and a given stock concentration, and covering a range of deviations for error parameters in order to compensate for systematic errors. The error parameters may include but are not limited to, effective flowrates, or effective flow cell heights, or effective diffusion constants. Said neural network is then used to determine the error parameters, and the results from a screen with respect to on- and off-rates.

Advantageously, by operating different injection pulses within the same injection sequence at different flowrates, mass transport effects can be distinguished from kinetic parameters.

Advantageously, the short contact times of the inventive method reduce the possibility of analytes to damage the ligands on the sensor surface, such as by non-specific binding or aggregation effects.

The invention claimed is:
1. A method for determining kinetic parameters of a reaction between analyte and ligands, the method comprising the steps of,
  (a) flowing a first volume of sample fluid (V1), which has a concentration ($c_o$) of analytes, over a test surface (3) of a flow cell (2) which has first ligands (4) attached thereto, for a first time period ($t_{1a}$), so that an analytes in said first volume of sample fluid (V1) can bind to the first ligands (4) on the test surface (3);
  (b) flowing a first volume of buffer solution (V1') over the test surface (3) of the flow cell (2), for a first time period ($t_{1b}$), to cause analyte from the first volume of sample fluid (V1), which bound to first ligands (4) on the test surface during step (a), to become dissociated from those ligands (4);
  (c) flowing at least a second volume of sample fluid (V2), over the test surface, for a second time period ($t_{2a}$), so that analytes in said second volume of sample fluid (V2) can bind to the first ligands (4) on the test surface (3); wherein the second time period ($t_{2a}$) is greater than the first time period ($t_{1a}$) and wherein the second volume of sample fluid (V2) has the same concentration ($c_o$) of analytes as the concentration ($c_o$) of analytes in the first volume of sample fluid (V2);
  (d) flowing a second volume of buffer solution (V2') over the test surface (3) of the flow cell (2), for a second time period ($t_{2b}$), to cause analyte from the second volume of sample fluid (V2), which bound to the first ligands

(4) on the test surface during step (a), to become dissociated from those first ligands (4);

(e) using a sensor to measure the binding on the test surface (3) during steps (a)-(d) to obtain a single measurement binding curve;

(f) flowing a first volume of sample fluid (V1), which has a concentration ($c_o$) of analytes, over a test surface (3') of a flow cell (2') which is without first ligands, for a first time period ($t_{1a}$);

(g) flowing a first volume of buffer solution (V1') over the test surface (3') which is without first ligands, for a first time period ($t_{1b}$);

(h) flowing at least a second volume of sample fluid (V2), over the test surface (3') which is without first ligands, for a second time period ($t_{2a}$); wherein the second time period ($t_{2a}$) is greater than the first time period ($t_{1a}$) and wherein the second volume of sample fluid (V2) has the same concentration ($c_o$) of analytes as the concentration ($c_o$) of analytes in the first volume of sample fluid (V2);

(i) flowing a second volume of buffer solution (V2') over the test surface (3') which is without first ligands, for a second time period ($t_{2b}$);

(j) using a sensor to measure the binding on the test surface (3') which is without first ligands, during steps (f)-(i), to obtain a single reference binding curve;

(k) using the single measurement binding curve and the single reference binding curve to determine the kinetic parameters.

2. A method according to claim 1 wherein the method is carried out using a first flow cell (2) which comprises a first test surface (3) which has first ligands (4) attached thereto, and a second flow cell (2') which comprises a second test surface (3') which is without first ligands; and wherein steps (a) and (f) are carried out simultaneously, and steps (b) and (g) are carried out simultaneously, and steps (c) and (h) are carried out simultaneously, and steps (d) and (i) are carried out simultaneously, and steps (e) and (j) are carried out simultaneously.

3. A method according to claim 1 wherein the method is carried out using a single flow cell which comprises a test surface, said test surface of the single flow cell is initially in a state in which it is without first ligands, and while the test surface is in a state in which it is without first ligands said steps (f)-(j) are carried out using said single flow cell;

wherein the method further comprises, after having carried out steps (f)-(j) then providing first ligands (4) on the test surface of the single flow cell;

after first ligands have been provided on the test surface of the single flow cell then carrying out steps (a)-(e) using said single flow cell.

4. A method according to claim 1 further comprising the steps of (a') flowing a first volume of sample buffer fluid ($V_{1B}$), over a test surface (3) of a flow cell (2) which has first ligands (4) attached thereto, for a time period ($t_{1B}$) which is equal to the first time period ($t_{1a}$) of step (a);

(b') flowing a first volume of buffer solution (V1') over the test surface (3) of the flow cell (2), for a time period which is equal to the first time period ($t_{1b}$) of step (b);

(c') flowing at least a second volume of sample buffer fluid ($V_{2B}$), over the test surface, for a second time period ($t_{2B}$) which is equal to the second time period ($t_{2a}$) in step (c);

(d') flowing a second volume of buffer solution (V2') over the test surface (3) of the flow cell (2), for a second time period which is equal to the second time period ($t_{2b}$) of step (d);

(e') using a sensor to measure the binding on the test surface (3) during steps (a')-(d') to obtain a single blank measurement binding curve;

(f') flowing a first volume of sample buffer fluid ($V_{1B}$) over a test surface (3') of a flow cell (2') which is without first ligands, for a time period ($t_{1B}$) which is equal to the first time period ($t_{1a}$) of step (f);

(g') flowing a first volume of buffer solution (V1') over the test surface (3) which is without first ligands, for a time period which is equal to the first time period ($t_{1a}$) of step (f);

(h') flowing at least a second volume of sample fluid (V2), over the test surface (3'), which is without first ligands, for a second time period ($t_{1B}$) which is equal to the second time period ($t_{2a}$) of step (h);

(i') flowing a second volume of buffer solution (V2') over the test surface (3') which is without first ligands, for a second time period which is equal to the second time period ($t_{2b}$) of step (i);

(j') using a sensor to measure the binding on the test surface (3) during steps (f')-(i') to obtain a single blank reference binding curve.

5. A method according to claim 4 further comprising the steps of (a") flowing a first volume of refractive index standard fluid ($V_{1s}$), over a test surface (3) of a flow cell (2) which has first ligands (4) attached thereto, for a time period ($t_{1s}$) which is equal to the first time period ($t_{1a}$) of step (a);

(b") flowing a first volume of buffer solution (V1') over the test surface (3) of the flow cell (2), for a time period which is equal to the first time period ($t_{1b}$) of step (b);

(c") flowing at least a second volume of refractive index standard fluid ($V_{2s}$), over the test surface, for a second time period ($t_{2s}$) which is equal to the second time period ($t_{2a}$) in step (c);

(d") flowing a second volume of buffer solution (V2') over the test surface (3) of the flow cell (2), for a second time period which is equal to the second time period ($t_{2b}$) of step (d);

(e") using a sensor to measure the binding on the test surface (3) during steps (a")-(d") to obtain a single measurement binding curve (smbc);

(f") flowing a first volume of refractive index standard fluid ($V_{1s}$) over a test surface (3') of a flow cell (2') which is without first ligands, for a time period ($t_{1s}$) which is equal to the first time period ($t_{1a}$) of step (f);

(g") flowing a first volume of buffer solution (V1') over the test surface (3) which is without first ligands, for a time period which is equal to the first time period ($t_{1a}$) of step (f);

(h") flowing at least a second volume of refractive index standard fluid ($V_{2s}$), over the test surface (3'), which is without first ligands, for a second time period ($t_{1s}$) which is equal to the second time period ($t_{2a}$) of step (h);

(i") flowing a second volume of buffer solution (V2') over the test surface (3') which is without first ligands, for a second time period which is equal to the second time period ($t_{2b}$) of step (i);

(j") using a sensor to measure the binding on the test surface (3) during steps (f")-(i") to obtain a single solvent reference binding curve.

6. A method according to claim 5 wherein step (k) comprises, subtracting the single reference binding curve (srbc) from the single measurement binding curve (smbc), to provide a difference curve;
subtracting the single blank reference binding curve (sbrbc) from the single blank measurement binding curve (sbmbc) to provide a blank difference signal;
zeroing the difference curve with respect to the y-axis by subtracting the average y-value of the difference curve at a zeroing time ty from the difference curve, to provide a zeroed single binding curve (zsbc);
zeroing the blank difference signal with respect to the y-axis by subtracting the average y-value of the blank difference signal at the zeroing time ty from the blank difference signal, to provide a zeroed single blank binding curve (zsbbc);
subtracting the zeroed single blank binding curve (zsbbc) from zeroed single binding curve (zsbc) to provide an adjusted binding curve (abc);
using the adjusted binding curve to determining said kinetic parameters.

7. A method according to claim 5 wherein step (k) comprises,
subtracting the single reference binding curve (srbc) from the single measurement binding curve (smbc), to provide a difference curve;
subtracting the single blank reference binding curve (sbrbc) from the single blank measurement binding curve (sbmbc) to provide a blank difference signal;
subtracting the single solvent reference binding curve (ssrbc) from the single solvent measurement binding curve (ssmbc) to provide a solvent difference signal;
zeroing the difference curve with respect to the y-axis by subtracting the average y-value of the difference curve at a zeroing time ty from the difference curve, to provide a zeroed single binding curve (zsbc);
zeroing the blank difference signal with respect to the y-axis by subtracting the average y-value of the blank difference signal at the zeroing time ty from the blank difference signal, to provide a zeroed single blank binding curve (zsbbc);
zeroing the solvent difference signal with respect to the y-axis by subtracting the average y-value of the solvent difference signal at a zeroing time ty from the solvent difference signal, resulting in a zeroed single solvent binding curve (zssbc);
carrying out solvent correction so as to provide a solvent corrected single blank binding curve ('scsbbc') and a solvent corrected single binding curve ('scsbc');
subtracting the solvent corrected single blank binding curve ('scsbbc') from the solvent corrected single binding curve ('scsbc') to provide an adjusted binding curve (abc);
using the adjusted binding curve to determining said kinetic parameters.

8. A method according to claim 7 wherein said solvent correction comprises, (i) determining average solvent difference ('sdiff'), by first determining solvent difference curve ('sdc') by subtracting the single solvent reference binding curve (ssrbc) from the single solvent measurement binding curve (ssmbc); and then determining the average value of solvent difference curve at a solvent time ts, wherein the average value of solvent difference curve at a solvent time ts is the average solvent difference ('sdiff'); (ii) determining the average value of the single solvent reference binding curve (srbc) at the solvent time ts;
(iii) repeating the steps of claim 5 to provide a plurality of different single solvent measurement binding curves and single solvent reference binding curves; and repeat steps (i) and (ii) for each of said plurality of different single solvent measurement binding curves and single solvent reference binding curves to yield a set containing average values of the single solvent reference binding curves ($srbc_i$) and a set of average solvent differences ($sdiff_i$);
(iv) determining a solvent correction function (fs) by fitting a polynomial function through the set to approximate sdiff=fs (srbc);
(v) obtaining a solvent corrected single binding curve (scsbc) by applying the solvent correction function (fs) to the single reference binding curve (srbc) and subtracting it from the zeroed single binding curve (zsbc) as follows:

scsbc=zsbc−$fs$(srbc);

(vi) obtaining a solvent corrected single blank binding curve (scsbbc) by applying the solvent correction function (fs) to the single blank reference binding curve (sbrbc) and subtracting the result from the zeroed single blank binding curve (zsbbc) as follows:

scsbbc=zsbbc−$fs$(sbrbc).

9. The method according to claim 7 wherein said solvent correction comprises
(i) determining the average value of the single solvent measurement binding curve ('smbc') at the solvent time ts
(ii) determining the average value of the single solvent reference binding curve ('srbc') at the solvent time ts
(iii) determining the average solvent difference ('sdiff') by subtracting the average value of the single solvent reference binding curve ('srbc') from the average value of the single solvent measurement binding curve ('smbc') according to the equation:

sdiff=smbc−srbc (iv) repeating the steps of claim 5 to provide a plurality of different single solvent measurement binding curves and single solvent reference binding curves; and repeat steps (i)-(iii) for each of said plurality of different single solvent measurement binding curves and single solvent reference binding curves to yield a set containing average values of the single solvent reference binding curves ($srbc_i$) and a set of average solvent differences ($sdiff_i$);
(v) determining a solvent correction function (fs) by fitting a polynomial function through the set to approximate sdiff=fs (srbc);
(vi) obtaining a solvent corrected single binding curve (scsbc) by applying the solvent correction function (fs) to the single reference binding curve (srbc) and subtracting it from the zeroed single binding curve (zsbc) as follows:

scsbc=zsbc−$fs$(srbc);

(vii) obtaining a solvent corrected single blank binding curve (scsbbc) by applying the solvent correction function (fs) to the single blank reference binding curve (sbrbc) and subtracting the result from the zeroed single blank binding curve (zsbbc) as follows:

scsbbc=zsbbc−$fs$(sbrbc).

10. The method according to claim 8 further comprising, obtaining a solvent corrected single solvent binding curve (scssbc) by applying the solvent correction function (fs) to the single solvent reference binding curve (ssrbc) and subtracting the result from the zeroed single solvent binding curve (zssbc) as follows:

$$scssbc = zssbc - fs(ssrbc).$$

11. A method according to claim 6 wherein the step of using the adjusted binding curve to determining said kinetic parameters comprises, fitting a model to the adjusted binding curve, wherein kinetic parameters of the model which best fit the adjusted binding curve are taken as said kinetic parameters of the reaction between the analyte in the first and second volumes of sample fluid (V1, V2) and the first ligands on the first test surface of the first flow cell.

12. A method according to claim 11, wherein said step of fitting a model to the adjusted binding curve comprises,
    determining an adjusted solvent curve (asc) by subtracting the single blank reference binding curve (sbrbc) from the single solvent reference binding curve (ssrbc);
    zeroing the adjusted solvent curve (asc) with respect to the y-axis by subtracting the average y-value of the adjusted solvent curve (asc) at the zeroing time ty from the blank difference signal, to provide a zeroed adjusted solvent curve (zasc)
    determining a single concentration curve by dividing the zeroed adjusted solvent curve (zasc) by an average maximum value of the zeroed adjusted solvent curve (zasc) to obtain a normalized solvent curve, and multiplying the normalized solvent curve by the concentration co of the analyte which was in the first and second volumes of sample fluid volumes (V1,V2);
    integrating the following differential equation using the single concentration curve as the variable 'c', and assuming initial guesses for the variables Rmax and the parameters ka and kd, to yield a simulated binding curve (sbc):

$$\frac{dR}{dt} = k_a c (R_{max} - R) - k_d R$$

determining the chi square ($\chi^2$) of the simulated binding curve (sbc);
    minimizing the chi square ($\chi^2$) to find the simulated binding curve which best fits the adjusted binding curve; wherein kinetic parameters of the simulated binding curve which best fits the adjusted binding curve are taken as said kinetic parameters of said reaction between the analyte and first ligands.

13. The method according to claim 11 wherein said step of fitting a model to the adjusted binding curve comprises,
    integrating the following differential equation using the single solvent reference binding curve (ssrbc) as the variable 'c', and assuming initial guesses for the variables Rmax and the parameters ka and kd, to yield a simulated binding curve (sbc):

$$\frac{dR}{dT} = k_a c (R_{max} - R) - k_d R$$

determining the chi square ($\chi^2$) of the simulated binding curve (sbc);
    minimizing the chi square ($\chi^2$) to find the simulated binding curve which best fits the adjusted binding curve; wherein kinetic parameters of the simulated binding curve which best fits the adjusted binding curve are taken as said kinetic parameters of said reaction between the analyte in the first and second volumes of sample fluid (V1,V2) and the first ligands on the first test surface of the first flow cell.

14. A method according to claim 4 wherein the method is carried out using a first flow cell (2) which comprises a first test surface (3) which has first ligands (4) attached thereto, and a second flow cell (2') which comprises a second test surface (3') which is without first ligands; and
    wherein steps (a') and (f') are carried out simultaneously,
    and steps (b') and (g') are carried out simultaneously,
    and steps (c') and (h') are carried out simultaneously,
    and steps (d') and (i') are carried out simultaneously,
    and steps (e') and (j') are carried out simultaneously.

15. A method according to claim 1 wherein all of said respective volumes of sample fluid which are flowed over the test surface of the flow cell, are aspirated from the same single receptacle before steps (a)-(k) are carried out.

16. A method according to claim 1 comprising flowing a plurality of volumes of sample fluid, all having the same concentration ($c_o$) of analytes, over the test surface of the flow cell; wherein the time duration which each volume of sample fluid flows over the test surface of the flow cell increases from one volume of sample fluid to the next.

17. A method according to claim 16 wherein, after each respective volume of sample fluid has been flowed over the test surface of the flow cell, flowing a volume of buffer solution over the test surface of the flow cell, to cause analyte which bound to first ligands on the test surface during the flowing of said respective volume of sample fluid over the test surface of the flow cell, becomes dissociated from those first ligands, wherein the time duration which each volume of buffer solution flows over the test surface increases from one volume of buffer solution to the next, so that the duration of time the first volume of buffer solution is flowed over the test surface of the flow cell is the shortest duration of time, and the duration of time the last volume of buffer solution is flowed over the test surface of the flow cell is the longest duration of time.

18. A method according to claim 17 wherein the shortest time duration which a volume of buffer solution flows over the test surface is shorter than three times a fall time of the analyte $\tau_a'$, where the fall time of the analyte $\tau_a'$ is the time from start of injection of the volume of buffer solution to the time the concentration of the analyte at the testing surface of the flow cell has reduced to an average concentration which is equal to or less than 5% of the concentration of the analyte in a volume of sample fluid.

19. A method according to claim 1 further comprising the step of identifying if the single measurement binding curve indicates that the amount of analytes bound to first ligands is below a predefined threshold; and if the amount of analytes bound to first ligands is not below a predefined threshold increasing the duration of time the last volume of buffer solution is flowed over the test surface of the flow cell until the single measurement binding curve indicates that the amount of analytes bound to first ligands is below the predefined threshold.

20. A method according to claim 1 wherein said first time period which the first volume of sample fluid is flowed over the test surface, is shorter than a rise time of the analyte $\tau_a$, wherein the rise time of the analyte $\tau_a$ is the time from start of injection of the analyte into the flow cell to the time the concentration of the analyte at the testing surface of the flow cell has reached an average concentration which is equal to or greater than 95% of the concentration of the analyte in the first volume of sample fluid.

* * * * *